US008586305B2

(12) United States Patent
Gurtner et al.

(10) Patent No.: US 8,586,305 B2
(45) Date of Patent: Nov. 19, 2013

(54) PROFILING OF CELL POPULATIONS

(75) Inventors: Geoffrey Gurtner, Stanford, CA (US); Michael Januszyk, Menlo Park, CA (US); Ivan Vial, Stanford, CA (US); Jason Glotzbach, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/516,195

(22) PCT Filed: Dec. 16, 2010

(86) PCT No.: PCT/US2010/060863
§ 371 (c)(1),
(2), (4) Date: Sep. 28, 2012

(87) PCT Pub. No.: WO2011/084643
PCT Pub. Date: Jul. 14, 2011

(65) Prior Publication Data
US 2013/0017968 A1  Jan. 17, 2013

Related U.S. Application Data

(60) Provisional application No. 61/287,044, filed on Dec. 16, 2009.

(51) Int. Cl.
*C12Q 1/68* (2006.01)
(52) U.S. Cl.
USPC .................... 435/6.1; 435/378; 536/24.31
(58) Field of Classification Search
None
See application file for complete search history.

(56) References Cited

U.S. PATENT DOCUMENTS

| 2007/0036765 A1* | 2/2007 | Civin et al. ................. 424/93.7 |
| 2007/0281313 A1 | 12/2007 | Taniguchi et al. |
| 2008/0124726 A1* | 5/2008 | Monforte ......................... 435/6 |
| 2008/0124756 A1 | 5/2008 | Dillon |

OTHER PUBLICATIONS

Diercks et al. (2009) PLoS One vol. 4: e6326, pp. 1-9.*
S. Kullback and R. Leibler, "On information and sufficiency," The Annals of Mathematical Statistics, vol. 22, No. 1, pp. 79-86 (Mar. 1951).
B. Efron, "Bootstrap methods: another look at the jackknife," Public Health Service Grant 5 R01 GM21215-02 Technical Report No. 32 (Jul. 5, 1977).
M. Goodell, K. Brose, G. Paradis, A.S. Conner, and R. Mulligan, "Isolation and functional properties of murine hematopoietic stem cells that are replicating in vivo," J Exp Med, vol. 183, pp. 1797-1806 (1996).

M. Eisen, P. Spellman, P. Brown, and D. Botstein, "Cluster analysis and display of genomewide expression patterns," Proc Natl Acad Sci USA, vol. 95, pp. 14863-14868 (Dec. 1998.).
T. Thorsen, S. Maerkl, andS. Quake, "Microfluidic large-scale integration," Science, vol. 298, pp. 580-584 (Oct. 2002).
M. Elowitz, A. Levine, E. Siggia, and P. Swain, "Stochastic gene expression in a single cell," Science, vol. 297, pp. 1183-1186 (Aug. 2002).
E. Ozbudak, M. Thattai, I. Kurtser, A. Grossman, and A. van Oudenaarden, "Regulation of noise in the expression of a single gene," Nature Genetics. vol. 31, pp. 69-73 (May 2002).
J. Levsky and R. Singer, "Gene expression and the myth of the average cell," Trends Cell Biol, vol. 13, No. 1, pp. 4-6 (Jan. 2003).
J. Paulsson, "Summing up the noise in gene networks," Nature, vol. 427, pp. 415-418 (Jan. 2004).
Y. Matsuzaki, K. Kinjo, R. Mulligan, and H. Okano, "Unexpectedly efficient homing capacity of purified murine hematopoietic stem cells," Immunity, vol. 20, pp. 87-93, (Jan. 2004).
Esch, "Prolog to Engineering in the Biological Substrate: Information Processing in Genetic Circuits," Proceedings of the IEEE, vol. 92, No. 5, pp. 846-847, (May 2004).
R. Tibshirani, G. Walther, "Cluster Validation by Prediction Strength," Journal of Computational and Graphical Statistics, vol. 14, No. 3, pp. 511-528 (2005).
I. Golding, J. Paulsson, S. Zawilski, and E. Cox, "Real-Time Kinetics of Gene Activity in Individual Bacteria," Cell 123, pp. 1025-1036 (2005).
A. Raj, C. Peskin, D. Tranchina, D. Vargas, and S. Tyagi, "Stochastic mRNA synthesis in mammalian cells," PLoS Biol, vol. 4, Issue 10, e309 (Oct. 2006).
C. Ramos, R. Bowman, N. Boles, A. Merchant, Y Zheng, I. Parra, S. Fuqua, C. Shaw and M. Goodell, "Evidence for diversity in transcriptional profiles of single hematopoietic stem cells," PLoS Genet, vol. 2, Issue 9, e159 (Sep. 2006).
L. Warren, D. Bryder, I. Weissman, and S. Quake, "Transcription Factor Profiling in Individual Hematopoietic Progenitors by Digital RT-PCR," Proc Natl Acad Sci USA vol. 103, No. 47, pp. 17807-17812 (Nov. 2006).

(Continued)

*Primary Examiner* — Jim Ketter
(74) *Attorney, Agent, or Firm* — Crawford Maunu PLLC

(57) ABSTRACT

Understanding the heterogeneity within a stem cell population remains a major impediment to the development of clinically effective cell-based therapies. Gene expression patterns exhibited by individual cells are a crucial component of this heterogeneity, yet transcriptional events within a single cell are inherently stochastic and can produce tremendous variability, even among genetically identical cells. It remains unclear how mammalian cellular systems overcome this intrinsic noisiness of gene expression to produce consequential variations in function. To address these questions, we utilized a novel single cell analysis method to characterize transcriptional programs across hundreds of individual murine long-term hematopoietic stem cells (LT-SCs). We demonstrate that multiple subpopulations exist within this putatively homogeneous stem cell population, defined by nonrandom patterns that are distinguishable from noise and can predict functional properties of these cells. This represents a powerful new tool to elucidate the relationship between transcriptional and phenotypic variation within a cell population.

15 Claims, 15 Drawing Sheets

(56) References Cited

OTHER PUBLICATIONS

Y. Karlen, A. McNair, S. Persequers, C. Mazza and N. Mermod, "Statistical Significance of Quantitative PCR," BMC Bioinformatics, vol. 8, No. 131 (Apr. 2007).

L. Warren, d. Rossi, G. Schiebinger, I. Weissman, S. Kim and S. Quake, "Transcriptional instability is not a universal attribute of aging," Aging Cell, vol. 6, pp. 775-782 (2007).

N. Maheshri and E. O'Shea, "Living with Noisy Genes: How Cells Function Reliably with Inherent Variability in Gene Expression," Annu Rev Biophys Biomol Struct, vol. 36, pp. 413-434, (2007).

M. Raaijmakers and D. Scadden, "Divided Within: Heterogeneity Within Adult Stem Cell Pools," Cell, vol. 135, pp. 1006-1008, (Dec. 2008).

A. Raj and A. van Oudenaarden, "Nature, Nurture, or Chance: Stochastic Gene Expression and Its Consequences," Cell, vol. 135, pp. 216-226, (Oct. 2008).

A. Wilson, E. Laurenti, G. Oser, R. van der Wath, W. Blanco-Bose, M. Jaworski, S. Offner, C. Dunant, L. Eshkind, E. Bockamp, P. Lio, H. R. MacDonald and A. Trumpp, "Hematopoietic Stem Cells Reversibly Switch from Dormancy to Self-Renewal During Homeostasis and Repair," Cell, vol. 135, pp. 1118-1129, (Dec. 2008).

I. Weissman and J. Shizuru, "The Origins of the Identification and Isolation of Hematopoietic Stem Cells, and Their Capability to Induce Donor-Specific Transplantation Tolerance and Treat Autoimmune Diseases," Blood, vol. 112, No. 9, pp. 3543-3553, (Sep. 2008).

I. Glauche, K. Moore, L. Thielecke, K. Horn, M. Loeffler and I. Roeder, "Stem Cell Proliferation and Quiescence—Two Sides of the Same Coin," PLoS Comput Biol, vol. 5, Issue 7, e1000447 (Jul. 2009).

M. Diehn, R. Cho, N. Lobo, T. Kalisky, M. Dorie, A. Kulp, D. Qian, J. Lam, L. Ailles, M. Wong, B. Joshua, M. Kaplan, I. Wapnir, F. Dirbas, G. Somlo, C. Garberoglio, B. Paz, J. Shen, S. Lau, S. Quake, J. M. Brown, I. Weissman, M. Clarke, "Association of Reactive Oxygen Species Levels and Radioresistance in Cancer Stem Cells," Nature, 458, pp. 780-783, (Apr. 2009).

T. Cagatay, M. Turcotte, M. Elowitz, J. Garcia-Ojalvo and G. Suel, "Architecture-Dependent Noise Discriminates Functionally Analogous Differentiation Circuits," Cell, vol. 139, pp. 512-522, (Oct. 2009).

A. Diercks, H. Kostner and A. Ozinsky, "Resolving Cell Population Heterogeneity:Real-Time PCR for Simultaneous Multiplexed Gene Detection in Multiple Single-Cell Samples," PLoS One, vol. 4, Issue 7, e6326, (Jun. 2009).

\* cited by examiner

PROFILING OF CELL POPULATIONS

RELATED PATENT DOCUMENT

This patent document is the national stage filing under 35 U.S.C. §371 of International Publication No. WO2011/084643 filed on Dec. 16, 2010, which claims the benefit, under 35 U.S.C. §119(e), of U.S. Provisional Patent Application Ser. No. 61/287,044 filed on Dec. 16, 2009, and entitled "Profiling of Cell Populations;" each of these patent documents is fully incorporated herein by reference.

FIELD OF INVENTION

The present invention relates to advances in quantification of gene expression within single cells.

BACKGROUND

There are currently many clinical trials for stem cell therapy underway worldwide that employ embryonic and adult stem cells. When using adult stem cells, the cells must first be isolated from the complex tissue of origin. The type of tissue from which adult stem cells can be isolated includes liver, heart, lung, adipose tissue, kidney, pancreas, bone marrow, and blood. Individual adult stem cells are isolated from complex tissue using fluorescence-activated cell sorting (FACS). FACS sorts cells, one cell at a time, based on the patterns of surface protein expression of each cell by incubating the cells with specific monoclonal antibodies that are conjugated to fluorescent molecules called fluorochromes. Theoretically, better results in clinical trials can be obtained by selection and administration of cells with certain surface protein expression patterns. The two main limitations of this selection method come from the fact that surface protein expression does not completely correlate with cell identity or function and that most groups of cells are heterogeneous in nature.

Gene expression profiling is a useful tool to define the identity and function of a group of cells, and can often provide more information than surface protein expression patterns alone. Selection of cells' for therapeutic use based on gene expression profiles offers significant advantages because this approach can define cell function more precisely. Methods of gene expression analysis include microarray, serial analysis of gene expression (SAGE), and polymerase chain reaction (PCR). More specifically, quantitative real time reverse transcriptase PCR (RT-PCR or qRT-PCR) is used to quantify the expression of a given gene or group of genes, which allows more precise comparison across samples. These methods are useful for defining the gene expression patterns of large populations of cells. In quantitative reverse transcriptase PCR, a messenger RNA strand is first reverse transcribed into cDNA, and then the resulting cDNA is amplified using real time/quantitative PCR (qPCR). This gives a quantitative assessment of the amount of RNA molecules for a specific gene within a cell or tissue as a measure of gene expression. Quantitative real time RT-PCR uses fluorescent probes that bind to DNA and allow for the visualization of the cDNA molecule as it is amplified during the PCR cycles. The point at which the probe becomes visible is precisely measured, which allows calculation of the amount of RNA from the gene of interest. The fluorescent signal produced from expression of each gene of interest is normalized against the signal from a reference gene measured in the same sample to account for possible variation in the amount and quality of RNA between different samples. Additionally, when many cells are analyzed as a single sample, the variances in gene expression among the cells cannot be analyzed because mRNA from all cells is pooled together. This population-averaging approach limits the ability of traditional analytic methods to define the gene expression patterns of a heterogeneous group of cells, such as stem cells.

SUMMARY

Various aspects of the present invention are directed toward assessing the similarities of stem cell populations in clinical trials and therapeutics, e.g., to verify that they are effectively the same across time and/or between institutions. Further aspects of the invention are directed toward quantifying the differences between cell populations and correlating those differences to observed clinical and therapeutic results. Still further aspects of the invention are directed toward choosing a cell population with the highest levels of favorable stem cells or the lowest levels of deleterious cells.

Consistent with one embodiment of the present disclosure, two cell populations are chosen for analysis. Multiple gene targets are chosen that will elucidate the transcriptional identity of each cell within the cell populations. Lysate from each individual cell undergoes reverse transcription followed by qPCR to quantify the gene expression for each gene target chosen. The gene expression is used to determine a transcriptional identity for each cell studied. The transcriptional identities of each cell are then used to determine a heterogeneity profile for each cell population as a whole. The heterogeneity profiles of the two cell populations are then compared to determine the similarity between the two populations.

Consistent with another embodiment of the present disclosure, a cell population is chosen for analysis. Multiple gene targets are chosen that will elucidate the transcriptional identity of each cell within the cell population. Lysate from each individual cell undergoes reverse transcription followed by qPCR to quantify the gene expression of each gene target chosen. The gene expression results are used to determine the transcriptional identity of each cell studied. The transcriptional identities of the cells are subject to clustering analysis to determine whether the cell population includes one or more possible subpopulations. The heterogeneity profiles of each of the subpopulations is determined, and then compared to confirm that each subpopulation is in fact a distinct subpopulation.

Consistent with yet another embodiment of the present disclosure, a cell population is chosen for analysis. The cell population contains a plurality of single cells. Multiple gene targets are chosen that will elucidate the transcriptional identity of each cell within the cell population. The gene expression level for each gene target chosen is determined. The transcriptional identity of each single cell is determined based on the gene expression level of the gene targets. A logic circuit is used to perform cluster analysis based on the transcriptional identity of each of the single cells of the cell population to determine whether the cell population includes one or more subpopulations. The heterogeneity profile of each subpopulation is determined A logic circuit is used to compare the heterogeneity profiles of each of the subpopulations to determine whether the subpopulations are distinct subpopulations. The total heterogeneity profile for the cell population is determined. A logic circuit is used to perform statistical analysis to compare the total heterogeneity profile of the cell population to a previously determined heterogeneity profile of a second cell population. Alternatively, the total heterogeneity profile of the cell population can be compared to a previously determined heterogeneity profile for the population to determine whether the cell population has changed over time.

The above summary is not intended to describe each embodiment of every implementation of the present disclosure. The figures and detailed description that follow more particularly exemplify various embodiments.

BRIEF DESCRIPTION OF THE DRAWINGS

The invention may be more completely understood in consideration of the detailed description of various embodiments of the invention that follows in connection with the accompanying drawings as follows:

FIG. 7-1 shows a histogram presenting raw qPCR cycle threshold values for a gene, according to an example embodiment of the present invention.

FIG. 7-2 shows a transcriptional distribution-based model of population homogeneity, according to another example embodiment of the present invention.

Figure 1:
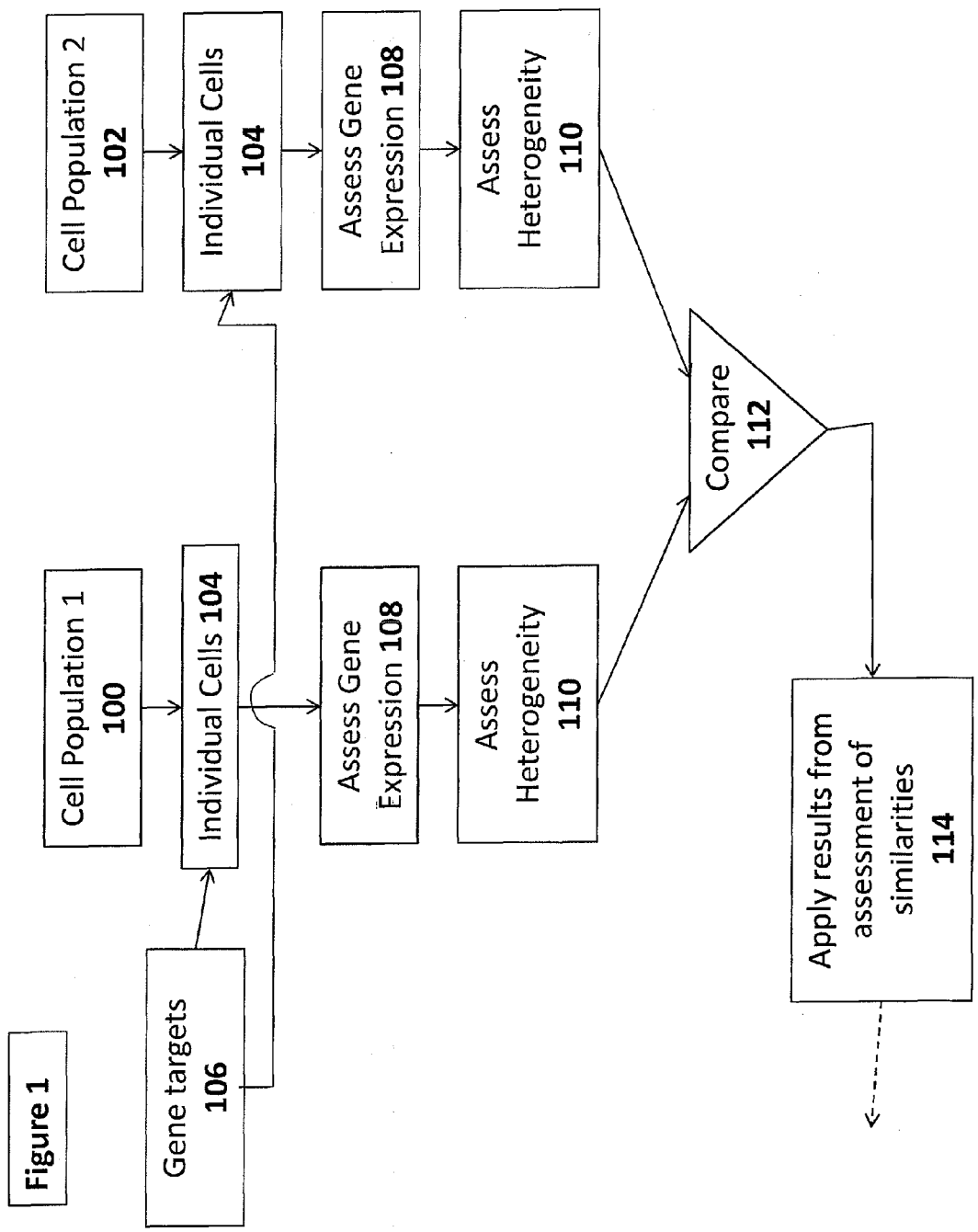
FIG. 1 shows a schematic of a comparison of two cell populations, according to an example embodiment of the present invention.

While the invention is amenable to various modifications and alternative forms, examples thereof have been shown by way of example in the drawings and will be described in detail. It should be understood, however, that the intention is not to limit the invention to the particular embodiments shown and/or described. On the contrary, the intention is to cover all modifications, equivalents, and alternatives falling within the spirit and scope of the invention.

DETAILED DESCRIPTION

The present invention is believed to be useful for applications involving comparing the gene expression of various cell populations. While the present invention is not necessarily limited to such applications, various aspects of the invention may be appreciated through a discussion of various examples using this context.

According to an example embodiment of the present disclosure, the similarity between two cell populations is determined by first isolating a plurality of single cells from a first cell population and a plurality of single cells from a second cell population. At least two individual genes are chosen to analyze an expression of the chosen genes within the single cells of each population. The transcriptional identity of each cell is determined based on the individual gene expression of the chosen genes within the cell. The transcriptional identity of the individual cells is used to determine a heterogeneity profile for a given cell population. Statistical analysis is performed by a logic circuit to compare the heterogeneity profile of the first cell population to the heterogeneity of the second cell population. The comparison between the two cell populations is used to determine the level of similarity between the two populations.

According to another example embodiment, the method for comparing gene expression includes isolating a plurality of single cells from a cell population. Multiple genes are chosen for which the expression of the genes within each of the individual cells is analyzed. A transcriptional identity is determined for each of the individual cells based on the level of gene expression of the chosen genes. A logic circuit is used to perform statistical analysis to determine whether the cell population includes one or more subpopulations based on the transcriptional identity of the single cells. The heterogeneity profiles of the one or more subpopulations are determined. A logic circuit is then used to determine whether the one or more subpopulations are distinct subpopulations based on the heterogeneity profiles.

According to another example embodiment, a plurality of single cells is isolated from a first cell population. At least two genes are chosen for expression within each of the single cells. The choice of genes is based in part on the type of cells believed to be in the cell population and/or the tissue from which the cell population was taken. A transcriptional identity of each of the single cells is determined based on the level of gene expression of the chosen genes. The transcriptional identity of the single cells is used to perform cluster analysis to determine whether the first cell population includes one or more subpopulations. The heterogeneity profiles of the one or more subpopulations are determined A logic circuit is used to perform statistical analysis to determine whether the one or more subpopulations are distinct subpopulations based on the heterogeneity profiles of each subpopulation. The total heterogeneity profile of the first cell population is determined based on the transcriptional identity of each of the single cells. A logic circuit is used to perform statistical analysis to compare the total heterogeneity profile of the first cell population to a previously determined heterogeneity profile of a second cell population.

The variability of clinical and laboratory results using FACS for specific markers to isolate stem cells suggest considerable cellular heterogeneity, even within specific marker profiles. Single cell analysis of gene expression can be slow, time-consuming, and limited to the study of a small number of genes. Certain embodiments of this disclosure are particularly useful for large scale rapid characterization of transcriptional profiles from single cells. Embodiments of this disclosure are also useful to interrogate a number of cells quickly. The study of multiple gene targets over multiple cells leads to very large data sets for each cell population. The complex nature of this data (both in number of gene targets and number of cells) is difficult to fully examine using the body of mathematical and statistical tools employed in traditional population-based analyses. It is desirable to be able to determine from the data the transcriptional heterogeneity within and among multiple cell populations. It is also desirable to be able to verify whether two populations, or subpopulations, are distinct.

For certain applications, one aspect of the present disclosure uses a microfluidics based approach that analyzes every cell of a given group of cells, which allows complete characterization of gene expression profiles within a group of cells. The information gained from this approach is not necessarily limited by the assumption that all cells isolated are relatively homogenous in their gene expression. This approach can overcome the assumption in that, if the isolated cells of interest are contaminated by surrounding cells or if they have variable levels of gene expression, then the individual nature of the analysis does not limit the information that can be gathered.

The heterogeneity of a given cell population is assessed using a phi-entropy based divergence analysis. Briefly, correlation coefficients are calculated for each pair of gene targets based on expression across cells in the population. An embodiment of the present disclosure uses Pearson product moment correlation coefficients, for example. In order to avoid artifacts due to data scaling, a shrinkage transformation is applied to the resulting matrix, with the shrinkage intensity determined according to sample size and variance. The entropy of the data is then computed for the modified covariance matrix about a multivariate lognormal probability density function for gene expression. In one embodiment, differential entropy, an extension of Shannon's entropy to continuous probability distributions, is computed. This provides a generalizable, indirect measure of information content and randomness based on maximum likelihood estimates, which functions as an absolute measure of heterogeneity for a population.

Embodiments of this disclosure are particularly useful for comparing the similarities of a two cell population. A divergence analysis is used to determine the amount of divergence between the probability distributions of the two cell populations. In one embodiment, an approach similar to symmetric Jenson-Shannon divergence is used. In another embodiment, when one population can be assumed to be the true reference, a Kullback-Leibler divergence is used. The Kullback-Leibler divergence allows for computation of the probability that the cells comprising one population came from the same larger distribution as the cells of a second population. In some embodiments divergence analysis is also used to evaluate the autonomy of any potential subpopulations (clusters) within one of the populations.

When using divergence analysis on populations (or subpopulations), if the subpopulations or populations are found to be highly divergent by the algorithm applied, then it is more likely the subpopulations or populations are distinct, rather than one large population displaying stochastic transcriptional variation. A bootstrapping approach is used to evaluate sample size and assess congruence across runs.

In order to normalize the gene expression profiles across multiple data sets, cycle threshold values for each gene are median-normalized and converted by the base 2 algorithm. Optimal model parameters such as cluster number, gene number and fuzziness coefficient are objectively determined using Akaike Information Criterion (AIC). This ensures the data is not over-fit and generally requires clustering on a limited subset. Genes are ranked according to their percent of variance using minimum distance estimation with a cutoff based on AIC. In an example embodiment of the present disclosure, a bootstrapped two-sample Kolmogorov Smirnov test is used. This provides objectively optimized clusters, whose autonomy may be objectively evaluated using the heterogeneity metric described above.

While several levels of regulation occur simultaneously within a cell in the progression from genome to protein production and cellular function, a cell's transcriptional program offers significant insight into a cell's identity and function. Complex tissues harbor heterogeneous groups of cells. The study of multiple genes across multiple single cells from a cell population allows for description of the cell population and the extent of its heterogeneity. This also allows for the recognition of rare cells, such as stem cells, within a complex tissue cell population. When patient-derived cell samples are being used for therapeutic administration, multiple samples can be evaluated and compared to select the one with the highest proportion of stem cells. Conversely, the comparison can be used to screen for the presence of potentially deleterious cells or oncogenic stem cell subsets within a population before therapeutic administration. The comparison can also be used to ensure that stem cell populations are substantially similar across time and/or between investigators when the populations are being used in clinical trials.

Referring to FIG. 1, two cell populations of interest 100 and 102 are chosen to be compared. Multiple gene targets 106 are chosen depending on the tissue type and the desired use of the cell populations. For each cell population, the cells are isolated in a single cell suspension and an individual cell 104 is sorted into each well of a multi-well plate. Each well of the plate can be pre-loaded with RT-PCR reagents. These RT-PCR reagents are reverse transcriptase and primers for each of the multiple gene targets 106 that have been chosen. In order to determine the level of gene expression 108 for each gene in each cell, a low cycle pre-amplification reverse transcriptase PCR (RT-PCR) step creates cDNA for each single cell across all gene targets. After the cDNA has been created, qPCR is performed on each individual cell 104 for each gene target 106, resulting in a number of data points. Statistical analysis, as described above, is then applied to the data generated from the gene expression to determine a transcriptional identity for each cell.

One time through the process of determining the gene expressions levels of each cell is called a run. In an embodiment of this disclosure, a run includes isolating cells and performing RT-PCR followed by qPCR. For a given run, the number of data points is the number of single cells tested multiplied by the number of gene targets being studied. In one embodiment, a 48×48 dynamic array chip is used. This allows for up to 48 cells and 48 genes to be studied. In another embodiment, a 96×96 dynamic array chip is used. The 96×96 chip allows for up to 96 cells and 96 genes to be studied. The dynamic array chips include thousands of integrated fluid channels, valve control surfaces, and reagent/reservoir chambers, all contained on a plastic chip.

Using the transcriptional identities of the cells, the heterogeneity 110 of each population is determined, and then the heterogeneity metrics 110 of each population are compared to one another using further statistical analysis 112. The results of this comparison can be used for a variety of applications 114. For example, the results of the divergence analysis may lead to the conclusion that the two populations are both subpopulations of a larger population of cells. If the cell populations tested are from two different investigators, this result would confirm that the populations are substantially similar. Conversely, if the divergence analysis indicated that the two populations were distinct, this would indicate that the cell populations, which had been previously thought to be from the same, larger cell population, are in fact different cell populations.

Figure 2:
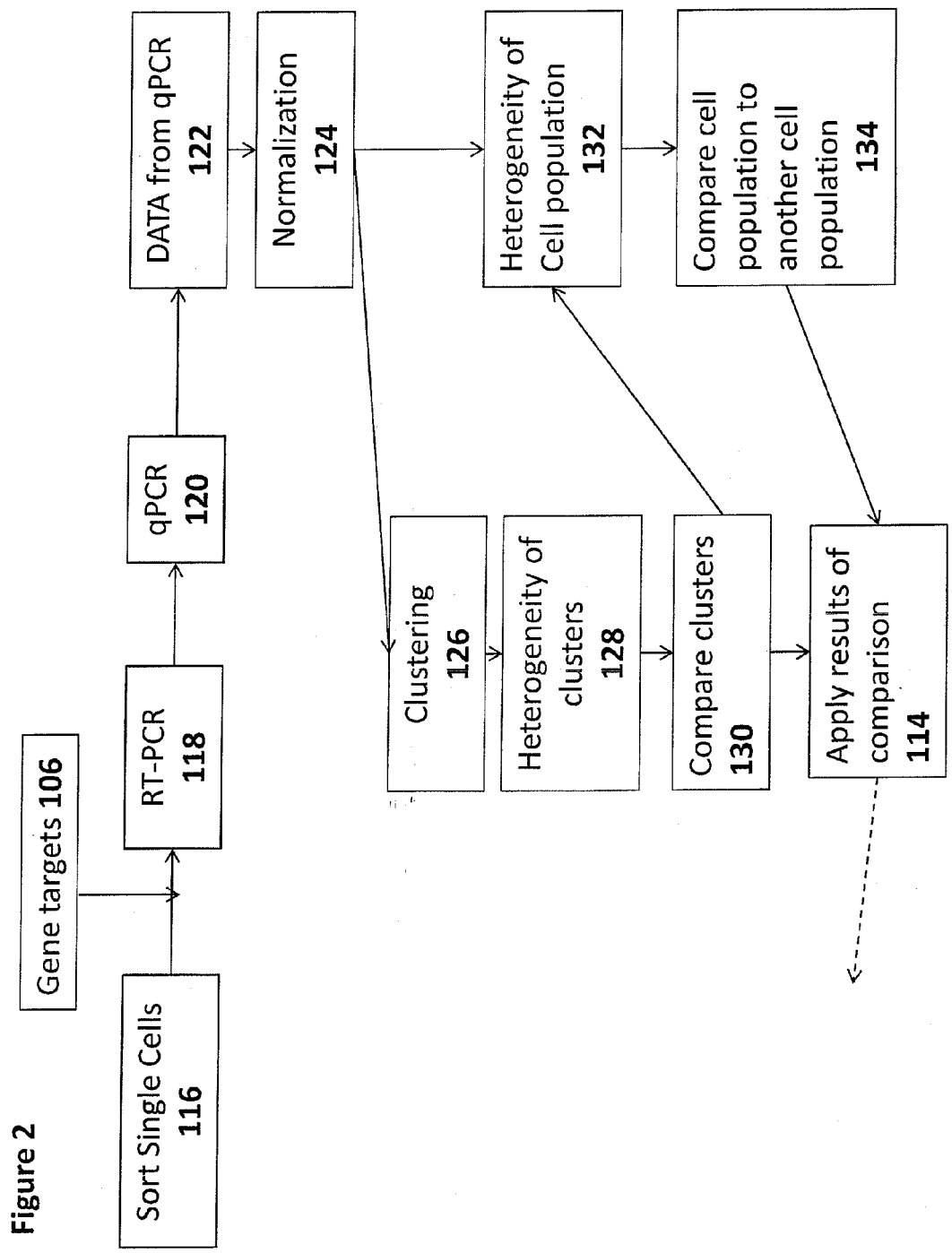
FIG. 2 shows a schematic of the determination of subpopulations, as well as comparison between populations, according to an example embodiment of the present invention.

FIG. 2 illustrates an alternative embodiment of the heterogeneity profile analysis. First, gene targets 106 are chosen to elucidate the transcriptional identity of each cell type within a cell population. The cells are isolated in a single cell suspension and sorted 116 so that a single cell is in each well of a multi-well plate. Each well is preloaded with RT-PCR reagents. The reagents include reverse transcriptase enzyme and primers for each of the chosen gene targets. Next, a low-cycle pre-amplification RT-PCR step 118 creates cDNA for each single cell across all gene targets. The single cell cDNA, along with a primer probe set for each gene target, is then subjected to qPCR 120 to quantify the amount of the gene expression of each gene target. This result is a gene expression number for each gene target within each cell. This data 122 is then normalized 124 so the gene expression profiles of each cell can be compared to the gene expression profiles of cells in different runs. This normalized data 174 can be used in two different ways. First, the data may be clustered using a clustering algorithm 126. The clustering algorithm 126 results in possible subpopulations. The autonomy of the identified clusters is then objectively evaluated using the heterogeneity metric 128 described above. For each possible subpopulation, a heterogeneity profile 128 is determined. The subpopulation's profiles are then compared 130. Depending on the level of divergence, the subpopulations are deemed to be either distinct cell populations, or simply two subpopulations of a larger coherent population. The normalized data 124 for the entire cell population tested can then be subjected to statistical analysis to determine the heterogeneity profile of the population as a whole 132. The heterogeneity profile 132 of the cell population is compared to heterogeneity profiles of previously studied cell populations 134. This allows for comparison both within the selected population, and between one or more separate populations. These results 114 can be used to, for example, evaluate multiple patent-derived cell samples in order to select the one with the highest proportion of stem-like cells for use in therapeutic administration.

Figure 3:
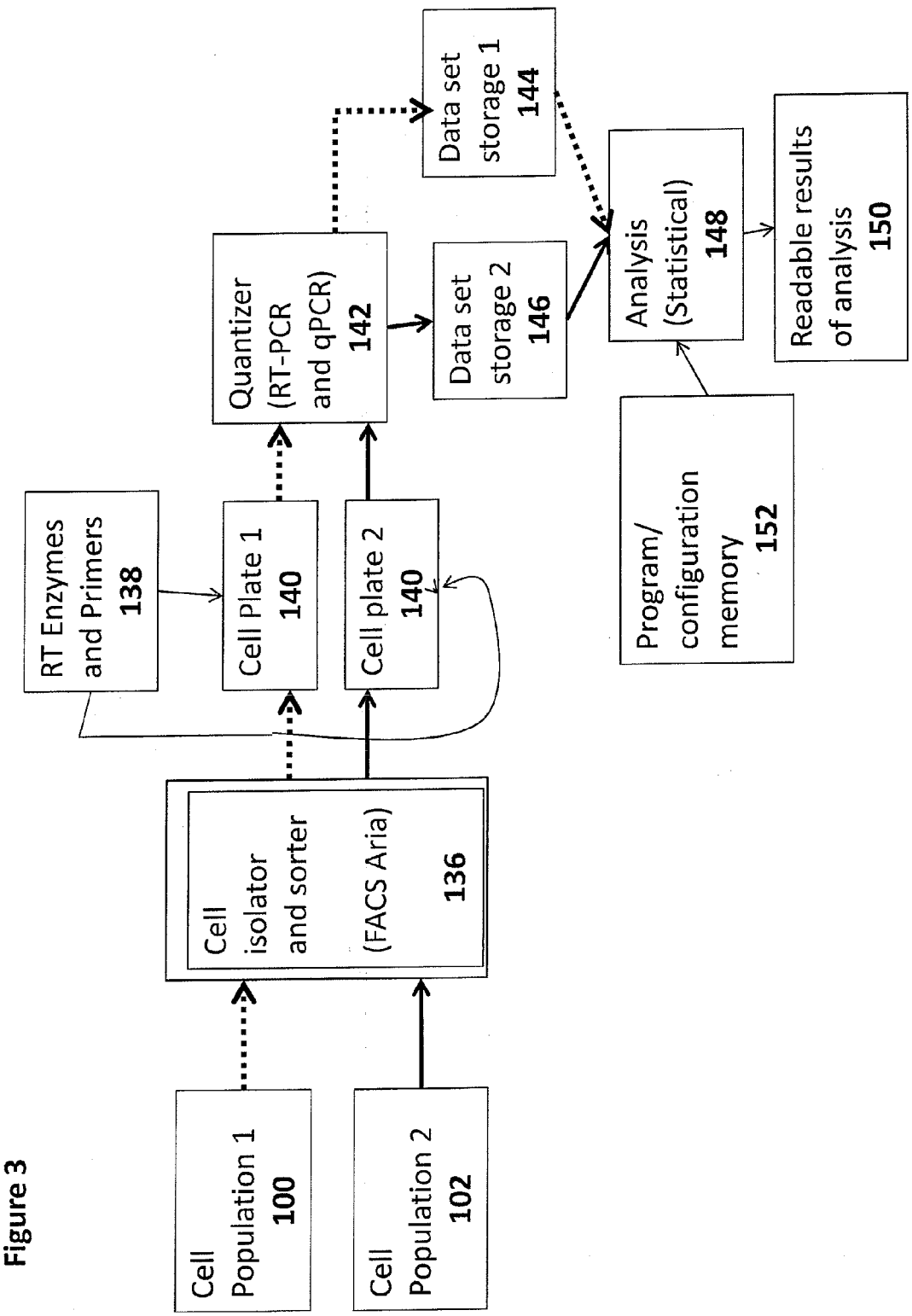
FIG. 3 shows a single cell fingerprinting system, according to an example embodiment of the present invention.

FIG. 3 shows a system through which a heterogeneity profile is derived. The cell populations of interest 100 and 102 are chosen. For the chosen cell types, multiple gene targets 106 (not shown in FIG. 3) that will elucidate the transcriptional identity of each cell type are chosen. The cell type of interest is isolated from a complex tissue of origin. Once the cells are isolated in a single cell suspension, the cells are stained with flow cytometry fluorescent antibodies and sorted into single cells using the FACSAria™ 136. A single cell is sorted into each well of a multi-well plate 140. Each well of the multi-well plate can been preloaded with reverse transcriptase enzymes and primers 138 for each of the selected gene targets 106. Low cycle pre-amplification reverse transcriptase PCR is preformed, creating cDNA for each single cell across all of the selected gene targets. The use of experimentally synthesized RNA standards for each gene allows for quantification of RNA copy number expressed by each cell in the analysis. The single cell cDNA is then loaded onto a microfluidics chip 140, along with the primer probe sets for the gene targets. This chip 140 is accepted by a quantizer 142, for example, the BioMark™ machine, which performs qPCR for each cell across all of the selected gene targets in parallel, resulting in numerous data points for each chip run. The output data set from the chip run is then stored in the data storage 144 of a computer, for example. The output of a second run is stored in a second data storage 146. The second data storage 146 can also contain data from previous chip runs. This allows for analysis 148 to occur at the time the run takes time when another sample is available for comparison. Statistical analysis takes place on a computer or other device capable of performing the required statistical analysis. The data is inputted into a program 152 which performs the various steps of the statistical analysis. The program outputs results 150 of the analysis that can be used in a variety of ways.

The analysis may be used to ensure that stem cell populations are substantially similar across time and/or between investigators. Stems cells are used in a variety of clinical trials. The analysis allows for the correlation between observed differences in clinical outcomes with specific transcriptional variations when two stem cell populations which were previously believed to be substantially similar are used. For the viability of stem cell based therapeutics, precise control over the content delivered is desirable, and minimizing (or controlling) the heterogeneity of the cell population leads to quality control. The comparison also allows for the determination of whether a cell population has changed its composition over time. Further, the technique can also be used in clinical trials when a high proportion of stem cells is desired, similar to when using the comparison to analyze cell populations for therapeutic administration.

Stems cells can be isolated from most differentiated tissues, including liver, heart, lung, adipose tissue, kidney, pancreas, bone marrow, and blood, all of which represent complex tissues with many heterogeneous cell types. Stem cell-based interventions have the potential to treat many diseases. For example, early results with mesenchymal stem cell treatment suggested improvement in myocardial recovery after infarction in animal models, which prompted several clinical trials using bone marrow-derived cells post-myocardial infarction.

Hierarchical and functional heterogeneity within a seemingly homogeneous population of cells has been observed often in biology. This theme occurs in both adult-derived and embryonic stem cells (ESCs). Gaining an understanding of the transcriptional profiles within multiple stem cell types will permit comparison of cells isolated by different protocols, different research groups, and different clinical sources to define their transcriptional identity on the single cell level. This approach will allow cell-based therapies to be subjected to similar quality control standards as pharmaceuticals. In addition, this technique of high-resolution transcriptional analysis also has the potential for significant impact on oncology and therapeutic safety, as defining specific transcriptional changes associated with malignant transformation in single cells will be feasible.

Experimental and/or Detailed Embodiments

Aspects of the disclosure are directed to a better understanding of the heterogeneity within a stem cell population for development of clinically effective cell-based therapies, related gene expression patterns exhibited by individual cells (and transcriptional events within a single cell and how mammalian cellular systems overcome this intrinsic noisiness of gene expression to produce consequential variations in function. To address such issues and in accordance with the present invention, a single cell analysis method is used to characterize transcriptional programs across hundreds of individual murine long-term hematopoietic stem cells (LT-HSCs). It is demonstrated that multiple subpopulations exist within this putatively homogeneous stem cell population, defined by nonrandom patterns that are distinguishable from noise and can predict functional properties of these cells. Unexpectedly, this represents a powerful new tool to elucidate the relationship between transcriptional and phenotypic variation within a cell population. To address how a single cell can generate a complex organism containing cells with diverse patterns of gene expression, it is appreciated that stochastic events can generate variations in patterns of expression among individual genetically identical cells, but that transcriptional patterns at the organism level are distinctly non-random (see, e.g., Maheshri, N. & O'Shea, E. K. Living with noisy genes: how cells function reliably with inherent variability in gene expression. *Annu Rev Biophys Biomol Struct* 36, 413-434 (2007). Single cell transcriptional stochasticity has been studied widely in bacteria and yeast (see, e.g., Newman, J. R. et al. Single-cell proteomic analysis of S. cerevisiae reveals the architecture of biological noise. *Nature* 441, 840-846 (2006)), but the effect of stochastic transcriptional patterns on mammalian stem cell heterogeneity remains unknown. Traditional gene expression analysis necessitates examination of pooled mRNA from thousands of cells, resulting in an averaged picture of gene expression across an entire cell population. Since the fundamental unit of biology is the single cell, studies have increasingly employed technologies for analyzing gene expression within individual cells. These studies have demonstrated that the transcriptional heterogeneity of individual cells must be addressed in order to adequately describe a cell population. In these regards, reference may be made to, Ramos, C. A. et al. Evidence for diversity in transcriptional profiles of single hematopoietic stem cells. *PLoS Genet* 2, e159 (2006); and Warren, L., Bryder, D., Weissman, I. L. & Quake, S. R. Transcription factor profiling in individual hematopoietic progenitors by digital RT-PCR. *Proc Natl Acad Sci USA* 103, 17807-17812 (2006).

Figure 4:
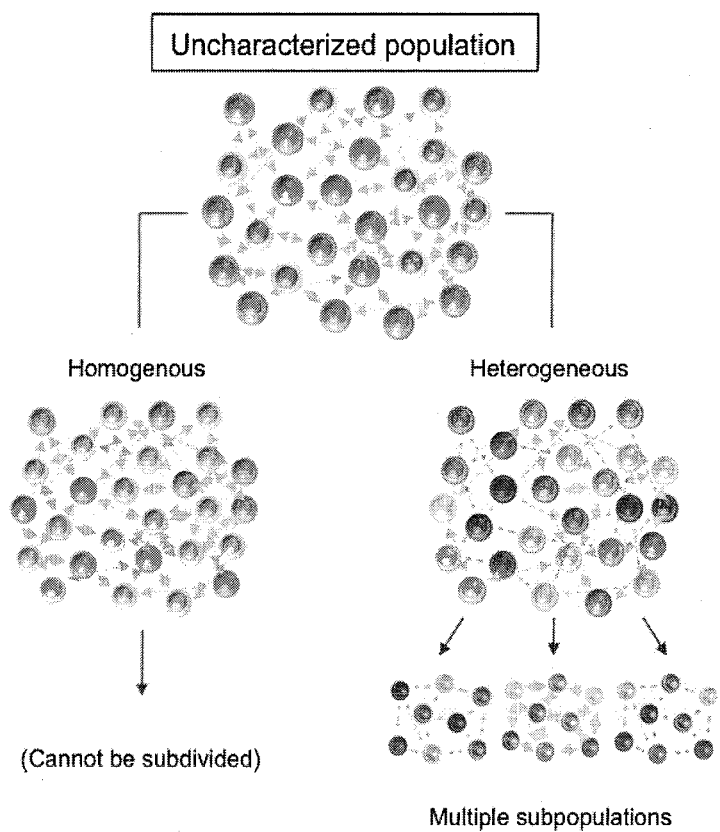
FIG. 4 illustrates a conceptual framework of transcriptional heterogeneity within a tightly sorted population of cells, consistent with an example embodiment of the present invention.

With reference to FIG. 4, the relationship between heterogeneous transcriptional profiles in a population of cells and stochastic variations of gene expression within individual cells can be better understood by using this illustrated conceptual framework of transcriptional heterogeneity within a tightly sorted population of cells. There likely exist several metastable and interconvertible transcriptional states of cells that combine to create a functionally heterogeneous population. Using precise single cell analysis, it is possible to determine whether the larger population of cells can be further subdivided into subpopulations that are different from each other, despite harboring a significant amount of stochastic variation within each subpopulation.

Bone marrow HSCs are an ideal system in which to explore the relationship between stochastic noise and meaningful variations in transcriptional profiles. In the bone marrow niche, cells exist as individual units, yet function collectively to create a complex hierarchical organ system (the blood). Each level of the canonical HSC lineage hierarchy has been defined, allowing prospective isolation of each cell type with a high degree of purity. At the pinnacle of this hierarchy, LT-HSCs exist as a putatively homogenous and largely quiescent population with the potential to generate all the cells of the hematopoietic system. However, the homogeneity of this compartment has been recently been called into question by the work of Wilson et al., which demonstrated that a tightly sorted LT-HSC population harbors significant functional heterogeneity with regard to cell cycling and stem cell capacity. The molecular basis for this heterogeneity cannot be elucidated from pooled populations of cells, but previous reports indicate that this requires single cell analysis. For background reference in these regards, reference may be made to: Weissman, I. L. & Shizuru, J. A., *The origins of the identification and isolation of hematopoietic stem cells, and their capability to induce donor-specific transplantation tolerance and treat autoimmune diseases*, Blood 112, 3543-3553 (2008); Glauche, I. et al. *Stem cell proliferation and quiescence—two sides of the same coin*, PLoS Comput Biol 5, e1000447 (2009); and Wilson, A. et al. *Hematopoietic stem cells reversibly switch from dormancy to self-renewal during homeostasis and repair*, Cell 135, 1118-1129 (2008).

We previously demonstrated that high-resolution single cell transcriptional analysis is efficient and reliable on a small scale using single cell fluorescence-activated cell sorting (FACS) and multiplexed quantitative polymerase chain reactions (qPCR) within a chip-based microfluidic large-scale integration system. See, e.g., Thorsen, T., Maerkl, S. J. & Quake, S. R., *Microfluidic large-scale integration*, SCIENCE 298, 580-584 (2002); Diehn, M. et al., *Association of reactive oxygen species levels and radioresistance in cancer stem cells*, Nature 458, 780-783 (2009).

In connection with the present disclosure, we significantly expand and refine this analytic method. We reproduced the sorting strategy used previously to define LT-HSCs (Wilson, A. et al., *Cell* 135, 1118-1129 (2008)) in order to isolate 300 individual cells from the CD34lo fraction of the LSK (lineage$^{neg}$ Sca-1$^+$ cKit$^+$) CD150$^+$ CD48$^-$ CD135$^-$ subset of primary murine bone marrow (as shown in FIG. 5a). For each of the LT-HSCs, we measured the expression of 43 genes (see Table 1 below) using a microfluidic-based method (FIG. 6). See Diehn, M. et al., *Association of reactive oxygen species levels radioresistance in cancer stem cells*, Nature 458, 780-783 (2009). Accordingly, FIG. 6 shows a schematic of high throughput microfluidic chip-based single cell transcriptional analysis. A single HSC was sorted into each well of a 96-well plate that had been preloaded with RT-PCR reagents (reverse transcriptase enzyme and primers for each gene target) using the FACSAria. A low-cycle RT-PCR pre-amplification step created cDNA for each gene target within each individual cell. Single cell cDNA was then loaded onto the microfluidics chip along with the primer-probe sets for the gene targets. The BioMark machine performed qPCR for each cell across all 48 gene targets in parallel, resulting in 2,304 data points for each chip run. A bioinformatics-based analysis was then applied to the dataset. This work represents the largest study to date of gene expression in single cells from a purified LT-HSC population, both in terms of the number of cells and number of genes analyzed.

Figures 1, 7:
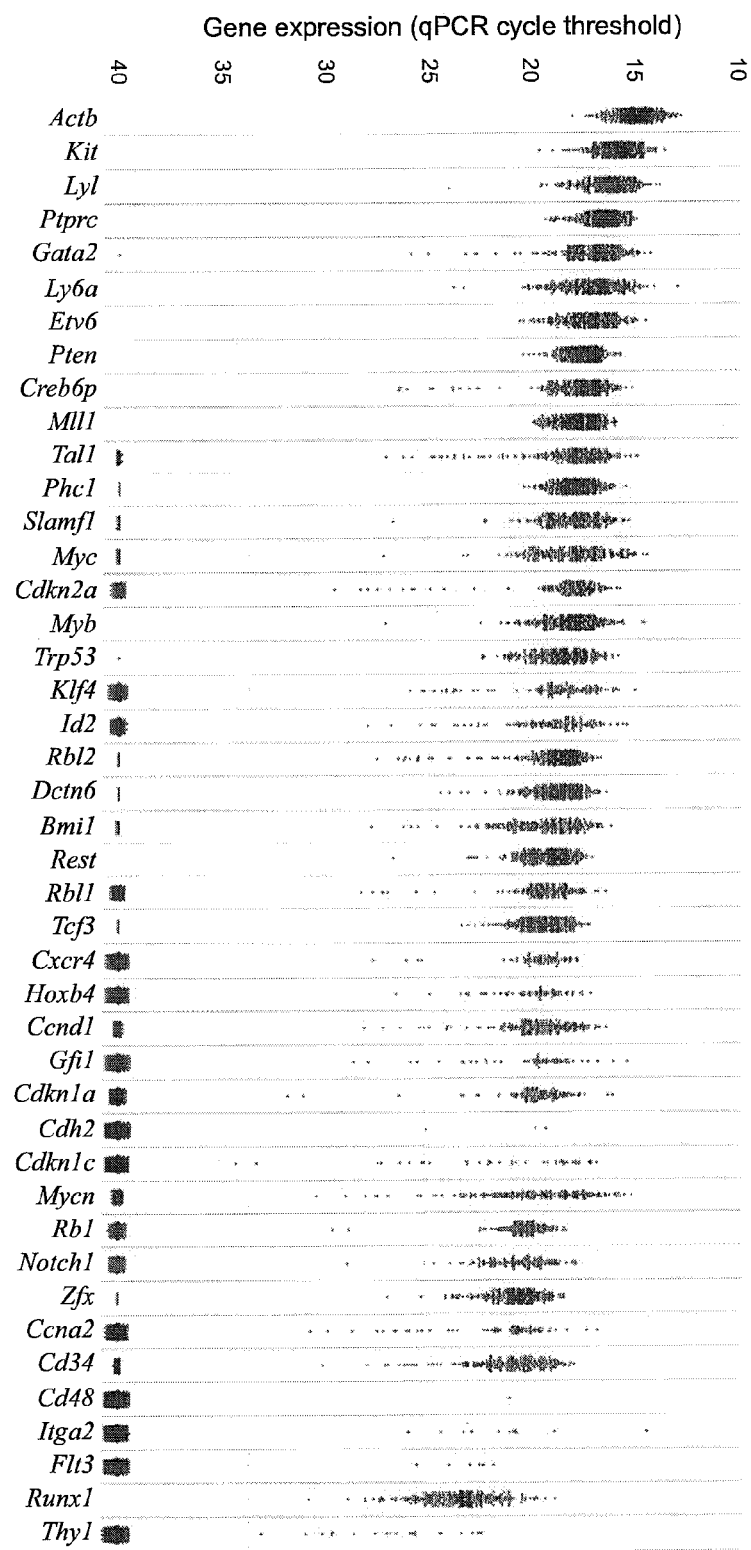
Figures 2, 7:
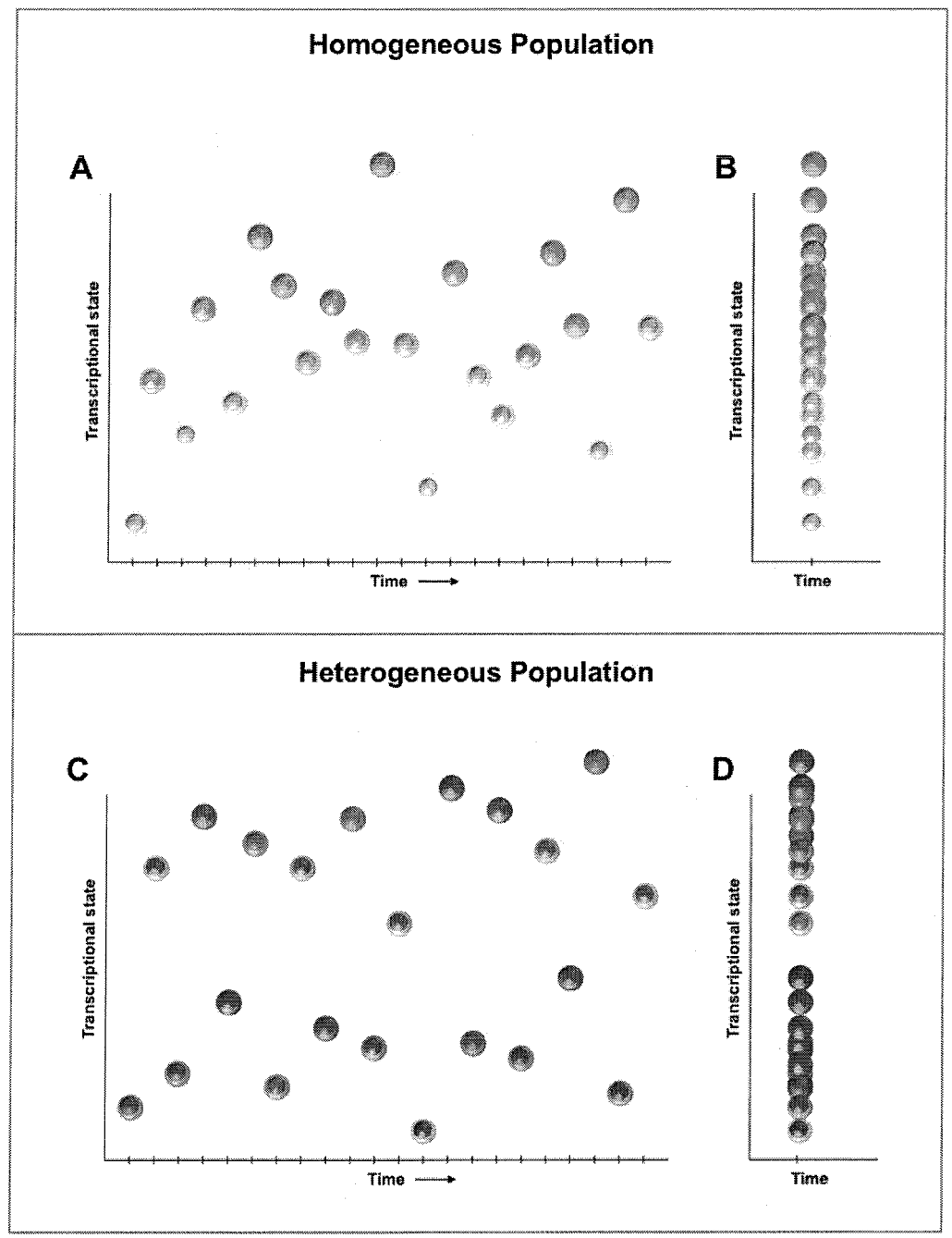

Cell-to-cell variation was observed in the expression of all genes (FIG. 5b and FIG. 7-1). Accordingly, FIG. 7-1 shows a histogram presenting raw qPCR cycle threshold values for each gene across all 300 LT-HSCs. Individual dots represent single gene/cell qPCR reactions, with increased cycle threshold values corresponding to decreased mRNA content. Cycle threshold values of 40 were assigned to all reactions that failed to achieve detectable levels of amplification within 40 qPCR cycles. The variation in expression followed a relatively normal distribution for many genes (e.g., the structural gene Actb, the hematopoietic surface antigen Ptprc, and the transcription factor Runx1). Such gene distributions exhibited a tendency for decreased relative transcriptional variation with increasing mRNA expression (FIG. 5c). However, some genes (e.g., the transcription factor Tal1 and the cell cycle-related genes Cdkn2a, Rbl1, and Ccnd1) displayed markedly asymmetric transcriptional distributions. These variations may be the result of transcriptional bursts as reported by others or could arise from physiological factors, such as discontinuities across the cell cycle.

We have previously shown that the univariate coefficient of variance (COV) can be used to describe single gene variability (see Equation 1, below and Warren, L. A. et al. *Transcriptional instability is not a universal attribute of aging*, Aging Cell 6, 775-782 (2007)). In connection with the present disclosure, the range of COV for individual genes (0.5 [Ptprc, also known as CD45] to 1.9 [Mycn]) (FIG. 5d) was consistent with that previously reported for murine HSCs (see, e.g., Warren, L. A. et al. (2007). If all variations in gene expression were independent (FIG. 5e), we could extend this analysis to construct a rudimentary index of population heterogeneity based on the multivariate generalization of COV over a given set of n genes (see Equation 2, below and Van Valen, L., *Multivariate structural statistics in natural history*, J Theor Biol 45, 235-247 (1974)).

$$cv = \frac{\sigma}{\mu} \quad (1)$$

$$cv_n = \frac{\sqrt{\sum_{i=1}^{n} \sigma_i^2}}{\sqrt{\sum_{i=1}^{n} \mu_i^2}} \quad (2)$$

Each $\sigma_i^2$ refers to a single gene variance, with $\mu_i$ representing its mean level of expression. The resulting dimensionless index ($cv_n$) would provide a standardized, scale-invariant measure of dispersion. However, this simple metric fails to account for co-variations among genes, which are present throughout our transcriptional data (FIG. 5e). Thus, a more comprehensive approach to evaluate heterogeneity within LT-HSCs is needed.

Aspects of the present disclosure address issues relating to cell-to-cell transcriptional variation relative to noise-generated fluctuations around a stable fixed point in a homogeneous population and to multiple eigenstates in a heterogeneous population. For further insight into the mechanisms of the cellular transcriptional machinery, particularly for regulatory feedback systems near equilibrium that would attenuate noise in data such as ours, our study measured transcription in 300 cells from a tightly sorted population at a single point in time. For background in this regard, see Cagatay, T., Turcotte, M., Elowitz, M. B., Garcia-Ojalvo, J. & Suel, G. M., *Architecture-dependent noise discriminates functionally analogous differentiation circuits*, Cell 139, 512-522 (2009).

We stipulate that a given population ($P_n$) of n cells (with transcriptomes $T_1, \ldots T_n$) is "homogeneous" if all individual cell transcriptomes are governed by identical steady-state probability functions (i.e., all cells are drawn from a single probability field). It follows that the transcriptional fingerprint of a homogeneous population measured at a single timepoint should recapitulate this single distribution through the transcriptional states of all individual cells (FIG. 7-2). Accordingly, FIG. 7-2 shows a transcriptional distribution-based model of population homogeneity. Given the noisiness inherent to transcription, an individual cell will exhibit a variable transcriptional signature if measured precisely over time (A). A cell population can be considered "homogeneous" if all individual cell transcriptomes are governed by identical steady-state probability functions (i.e. all cells are drawn from a single probability field). It follows that the transcriptional fingerprint of a homogeneous population measured at a single timepoint (B) should, through the transcriptional states of all individual cells, recapitulate the single distribution observed for any one cell measured across multiple time points (A). By contrast, if the distribution of individual cell transcriptomes from a population at a single timepoint (D) more closely reflect that of two (or more) independent probability functions (C), then the population may be designated as heterogeneous. Thus, establishing the homogeneity of $P_n$ is equivalent to demonstrating that no set of subpopulations $P'_s = P_n$ exists for which the observed data ($T_1, \ldots T_n$) are more likely to have arisen from their joint probability distribution than from $P_n$ itself. We applied this paradigm to our multivariate system of gene expression in order to evaluate the heterogeneity of a highly purified population of LT-HSCs.

In order to determine whether LT-HSCs (FIG. 8a) represent a homogeneous population or several discrete subpopulations, we applied a unifying procedure for model selection and multimodal inference based on the principles of information divergence, originally described by Kullback and Leibler. Initial feature selection was achieved through non-parametric two-sample Kolmogorov-Smirnov testing of $CD34^{lo}$ cells against a population of otherwise identically sorted $CD34^{hi}$ HSCs (FIG. 5a), which have been shown to harbor a much lower stem cell capacity. This analysis identified a subset of nine genes with distributions of expression that were different between the two cell populations (p<0.01 after applying Bonferroni correction for multiple comparisons) (FIG. 8b, c). We then applied a generalized fuzzy c-means clustering algorithm, which permits partial memberships via "soft partitions" representing overlap in probability distributions (see FIG. 8d and Kerr, G., Ruskin, H. J., Crane, M. & Doolan, P., *Techniques for clustering gene expression data*, Comput Biol Med 38, 283-293 (2008)). This method is parametric with respect to cluster number and fuzziness coefficient. We utilized an information metric, Akaike Information Criterion (AIC), to assess the "goodness of fit" for each parameterization across fuzzy- and cluster-space in order to optimize clustering parameters and minimize information loss (FIG. 8e). This permits robust, objective comparison of the single-cluster model against all permutations of multi-cluster alternatives (see Kullback & Leibler).

Although AIC itself is poorly suited to traditional null hypothesis testing, multiple methods have been developed to evaluate uncertainty in model selection (see, e.g., Burnham, K. P. a. A., D. R. *Model selection and multimodal inference: a practical information-theoretic approach*, Edn. 2nd. (Springer Science, New York; 1998)). We computed AIC differences, Akaike weights, and evidence ratios for each clustering parameter (see Table 2) to examine differences among the canonical one-cluster model, the "optimal" three-cluster model as determined by our method, and other cluster arrangements (FIG. 8e and Table 2). Our results demonstrate that it is more likely that these highly purified cells exist in distinct subpopulations rather than as one homogeneous population, suggesting the presence of true heterogeneity within the LT-HSC compartment.

In the optimal partitive model, CD34$^{lo}$ HSCs distributed relatively evenly across three clusters, each with distinctive transcriptional fingerprints (see FIG. 9a). The number of clusters was found to be relatively stable against changes in cell selection, gene selection, gene number, and clustering algorithm (FIGS. 10a-f and 11).

FIGS. 10a-f show an evaluation of cluster stability. We evaluated the stability of our cluster-based approach with respect to changes in parameterization and dataset composition. (FIG. 10a) Bootstrapping was employed to evaluate 10,000 randomly selected subsets (70% [210 cells]) of our LT-HSC data. The AIC-optimal number of clusters varied from 2 to 4 across all iterations (mean=2.87; std. dev.=0.52), with an optimal model of 3 clusters selected in 71.8% of all permutations. Mean AIC values for each number of clusters (solid line) are depicted, with dashed lines delimiting one standard deviation. (FIG. 10b) We repeated our analysis using an alternate method for gene selection, choosing; the nine genes with highest coefficients of variation. The AIC-optimal model again consisted of three clusters, similar but not identical to those chosen with the earlier method. (FIG. 10c-d) Repeat analyses using the 8 (c) or 10 (d) genes with highest coefficients of variation, resulting in similar AIC-optimal models. (10e) Information loss as a function of cluster number for the data in FIGS. 10b-d (solid lines), compared with that from FIG. 10a (dashed line). (FIG. 10f) Information loss as a function of cluster number using gene selection based on Kolmogorov-Smirnov significance (FIG. 8b).

Figure 11:
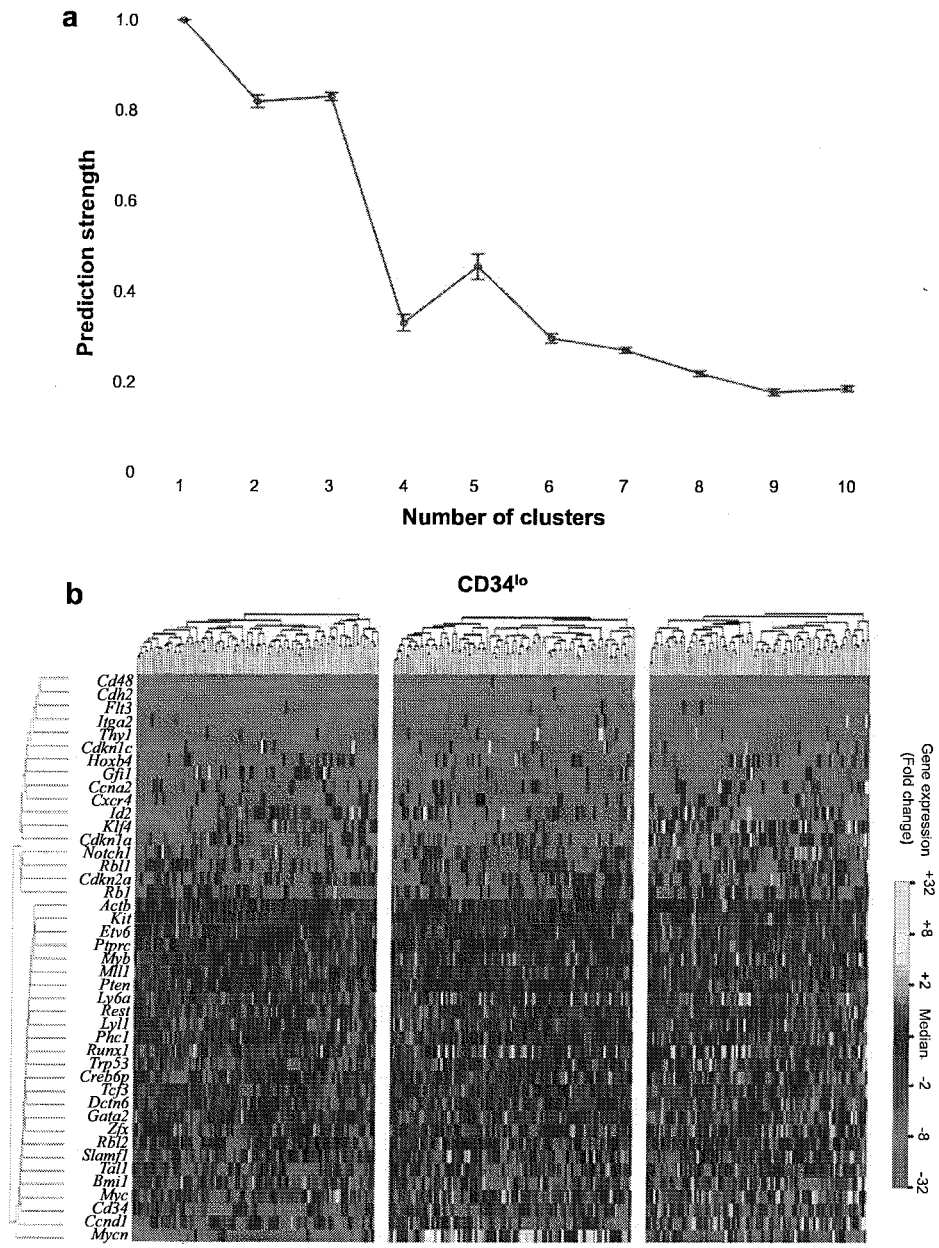
FIG. 11 (via related FIGS. 11a-11b) illustrates a robustness analysis with respect to clustering technique, consistent with another example embodiment of the present invention.

FIG. 11 illustrates a robustness analysis with respect to clustering technique. Having demonstrated the stability of our approach with respect to changes in data and parameterization, we evaluated whether our findings could be artifacts of the approach itself. As no true precedent exists for data analysis of this type, we re-examined our data using the most simple form of partitional analysis (k-means clustering), in conjunction with a supervised classification method well-suited for clustering high-dimensional data without the need for feature selection (i.e., a gene subset) to reduce the number of free parameters (see FIG. 11a and Tibshirani R., W., G., *Cluster Validation by Prediction Strength*, Journal of Computational and Graphical Statistics 14, 511-528 (2005)). Gene expression data for all 300 LT-HSCs were evaluated using a generic k-means algorithm, and the prediction strength of each k (number of clusters) calculated using five-fold cross-validation over 100 iterations as previously described. Cluster validation was achieved by maximizing the fidelity of pair-wise co-memberships of cells within clusters across repeated sub-samplings. The appropriate number of clusters was determined by the largest k whose prediction strength exceeds a certain threshold (typically set at 0.8); see Tibshirani (2005). See also FIG. 11b. Optimal partitioning of LT-HSCs using k-means, with k=3 clusters as determined above.

For these analyses, certain genes (for example, Mycn and Cdkn2a) consistently showed high expression associated with specific clusters, whereas other genes (for example, Runx1 and Myb) exhibited stochastic variation among clusters (FIG. 9a and FIG. 10b, c, d). Thus, our results suggest the presence of both stochastic and nonstochastic variations in gene expression.

Figure 9:
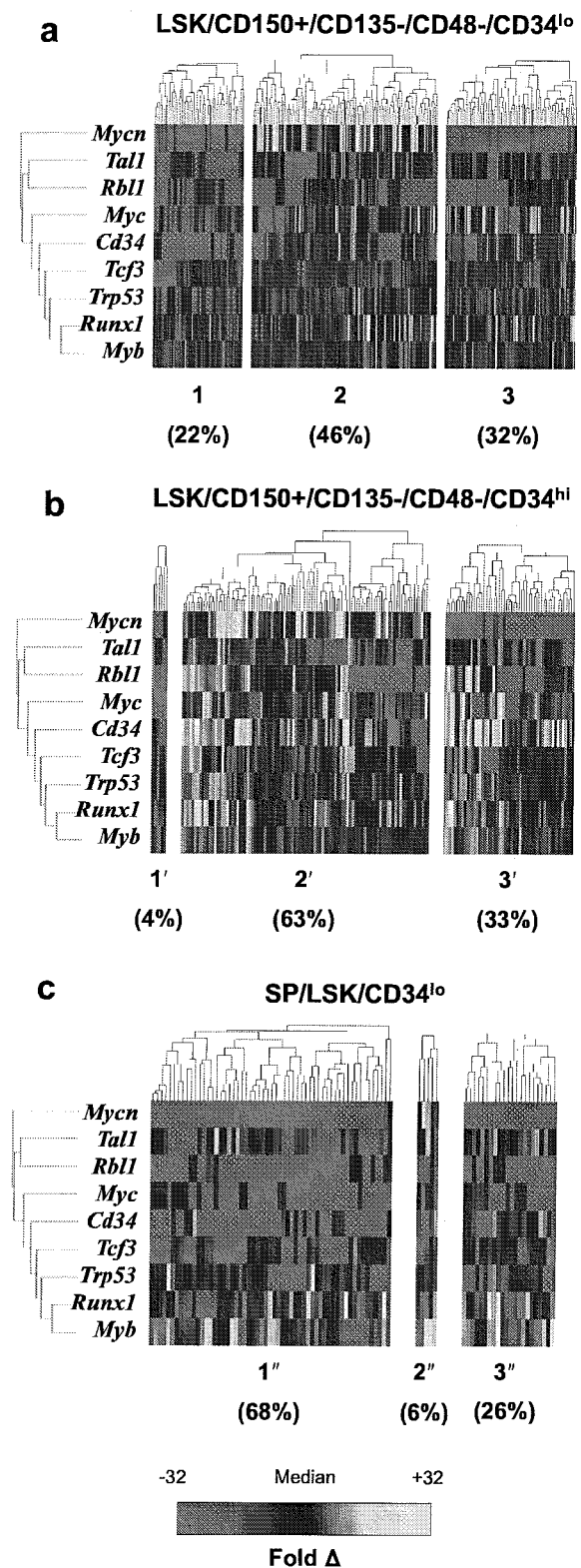
FIG. 9 shows the results of optimized partitive modeling of HSC (hematopoietic stem cell) single cell transcriptional data, according to another example embodiment of the present invention.
Figure 12:
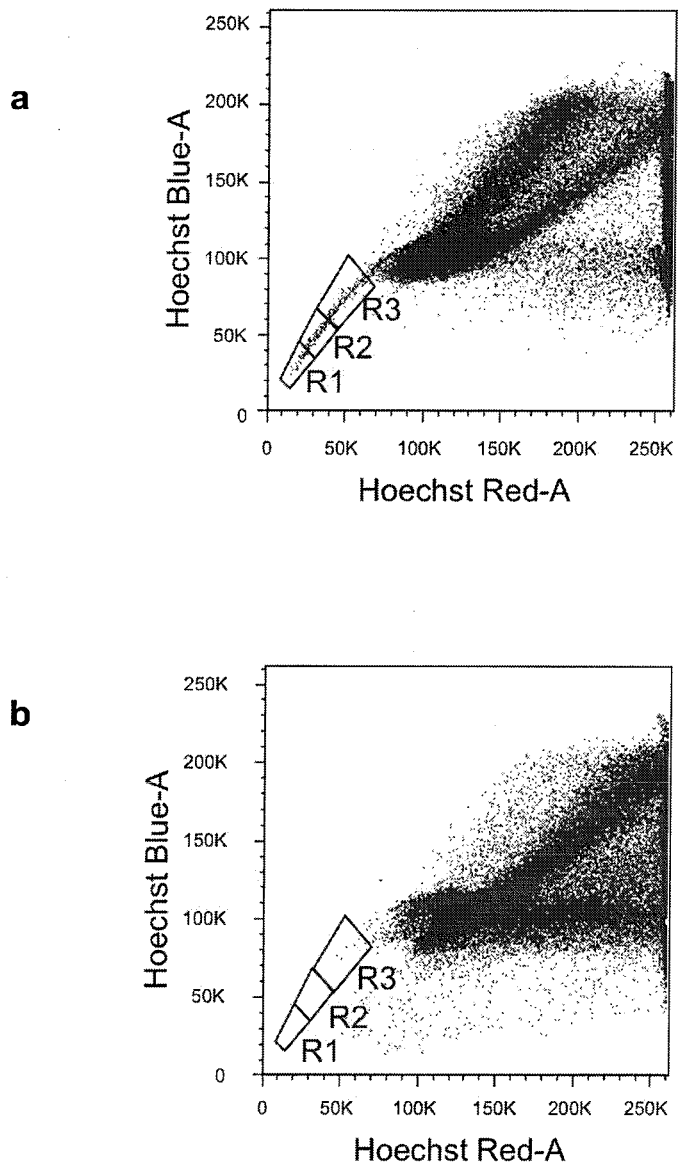
FIG. 12 (via related FIGS. 12a-12b) shows FACS plots for murine stem cell experiments, according to an example embodiment of the present invention.

We organized the CD34$^{hi}$ HSCs around the cluster centroids generated through the clustering of CD34$^{lo}$ HSCs (FIG. 9a), and observed a dramatically different distribution across these three clusters (FIG. 9b). CD34$^{lo}$ HSCs have been shown by others to contain a much larger subset of dormant LT-HSCs with a high stem cell capacity in comparison to CD34$^{hi}$ HSCs (see Wilson, A. P t al. (2008). Thus, it is possible that the different clusters identified by our analysis reflect subpopulations that account for the observed functional differences between these two HSC populations. To test this relationship, we utilized an alternate isolation protocol for LT-HSCs that yields a side population (SP) based on cellular Hoechst dye 33342 extrusion (FIG. 12); see Matsuzaki, Y., Kinjo, K., Mulligan, R. C. & Okano, H., *Unexpectedly efficient homing capacity of purified murine hematopoietic stem cells*, Immunity 20, 87-93 (2004); and Goodell, M. A., Brose, K., Paradis, G., Conner, A. S. & Mulligan, R. C., *Isolation and functional properties of murine hematopoietic stem cells that are replicating in vivo*, J Exp Med 183, 1797-1806 (1996). Thus, FIG. 12 shows representative FACS plots for murine stem cell experiments. (FIG. 12a) FACS plots of LT-HSC isolation using Hoechst dye extrusion (side population method), with three side population subfractions delineated (R1-R3), as previously reported. Side population "tip" cells (R1) were isolated from lineage cell-depleted murine bone marrow cells and further sorted for lineage negative, cKit positive, Sca-1 positive, CD34$^{lo}$ cells using identical gates to those presented in FIG. 4. (FIG. 12b) Abrogation of side population cells after incubation with verapamil 50 μM and Hoechst 33342. When organized around the same cluster centroids, 68% of the SP LSK CD34$^{lo}$ cells were associated with cluster 1 (FIG. 9c). Taken together, these findings suggest that LT-HSC capacity may exist within a subpopulation of cells that are largely absent from the CD34hi population (cluster 1 of FIG. 9) and that additional surface marker sorting will be needed to isolate a homogeneous population of LT-HSCs.

Our results demonstrate the feasibility of measuring gene expression in multiple individual cells from a stem cell population using single cell quantitative reverse transcription polymerase chain reaction (qRT-PCR) in a multiplexed array based on microfluidic large-scale integration. Using this approach, we detected variations in gene expression profiles within a well-studied murine LT-HSC population that could not be accounted for by stochastic transcriptional noise alone. Specifically, we identified several transcriptionally defined subpopulations that were consistent with the known functional heterogeneity of LT-HSCs. It is important to note that post-transcriptional factors such as mRNA translation or protein modification may serve to mitigate (or amplify) the impact of this heterogeneity. Nevertheless, our data suggest that variations in gene expression define subpopulations within LT-HSCs and that the development of new sorting parameters may permit further enrichment of hematopoietic stem cells. More broadly, these findings demonstrate the utility of such an approach to define the transcriptional organization of complex cell populations.

Further Discussion of Figures for Experimental/Detailed Embodiments

Figure 5:
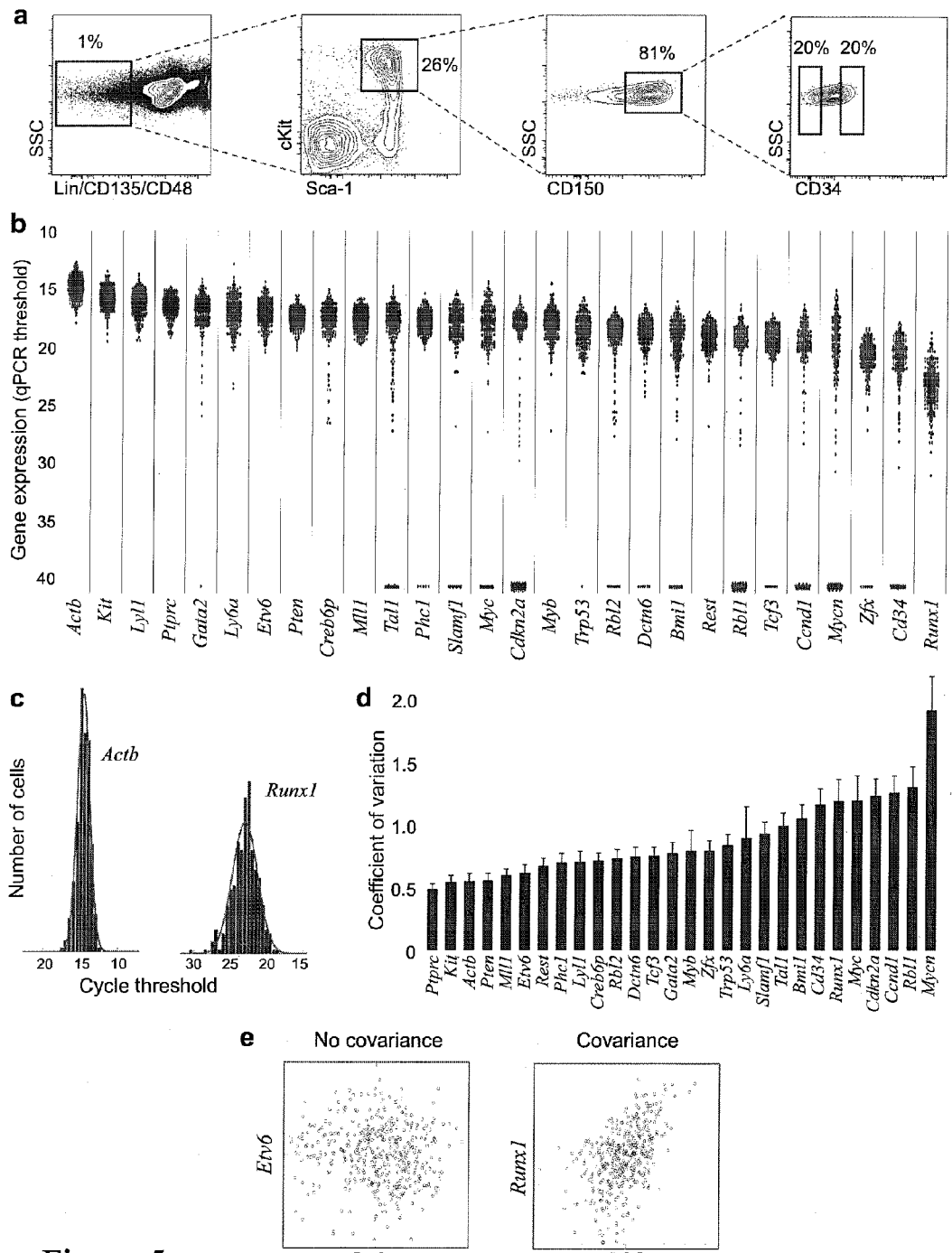
FIG. 5 (via related FIGS. 5a-5e) illustrates single cell gene expression analysis, according to another example of the present invention.
Figure 6:
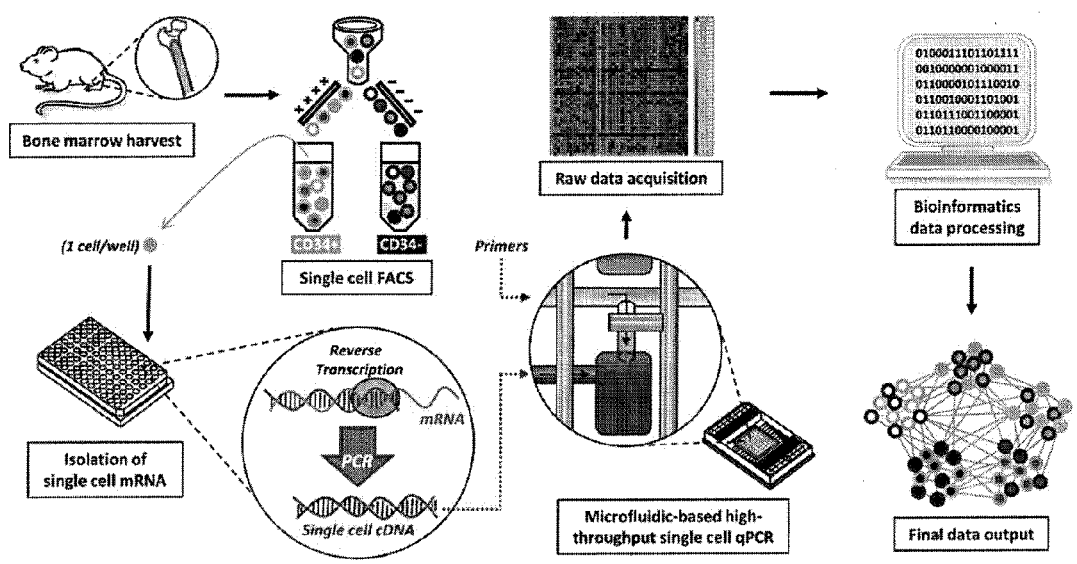
FIG. 6 shows a schematic of high throughput microfluidic chip-based single cell transcriptional analysis, consistent with an example embodiment of the present invention.

FIG. 5 shows single cell gene expression analysis that demonstrates transcriptional variation in murine LTHSCs. (FIG. 5a) FACS sorting parameters of two populations of HSCs isolated from primary murine bone marrow. All cells were LSK (Lin$^{neg}$ Sca-1$^+$ cKit$^+$) CD150$^+$ CD135$^-$ CD48$^-$ and were sorted into two distinct populations based on CD$^{34}$ expression (CD34$^{lo}$ and CD34$^{hi}$). SSC=side scatter. (FIG. 5b) Histogram presenting raw qPCR cycle threshold values for individual genes across all 300 LT-HSCs. Each dot represents a single gene/cell qPCR reaction, with increased cycle threshold values corresponding to decreased mRNA content. Cycle threshold values of 40 were assigned to all reactions that failed to achieve detectable levels of amplification within 40 qPCR cycles. For convenience, genes that failed to amplify in the majority of cells have been omitted (see FIG. 7-1 for full data). (FIG. 5c) Lognormal distribution of mRNA messages of Actb and Runx1 across individual CD34$^{lo}$ HSCs. (FIG. 5d) Single gene coefficient of variance (COV) values for individual CD34$^{lo}$ HSCs. Error bars represent standard deviations derived through bootstrapping over 100,000 iterations as previously described. (FIG. 5e) Interaction between expression of two genes, represented on the horizontal and vertical axes. The genes Etv6 and Ly6a (left panel) exhibit the weakest transcriptional covariance of all gene pairs, and their expression is nearly independent. However, many gene pairs, such as Runx1 and Myb (right panel), exhibit strong positive covariance, whereby increased expression of one gene is associated with increased expression of the other. In this case, the assumption of independent gene expression does not hold, suggesting that a rudimentary COV analysis cannot fully describe multi-gene heterogeneity.

Figure 8:
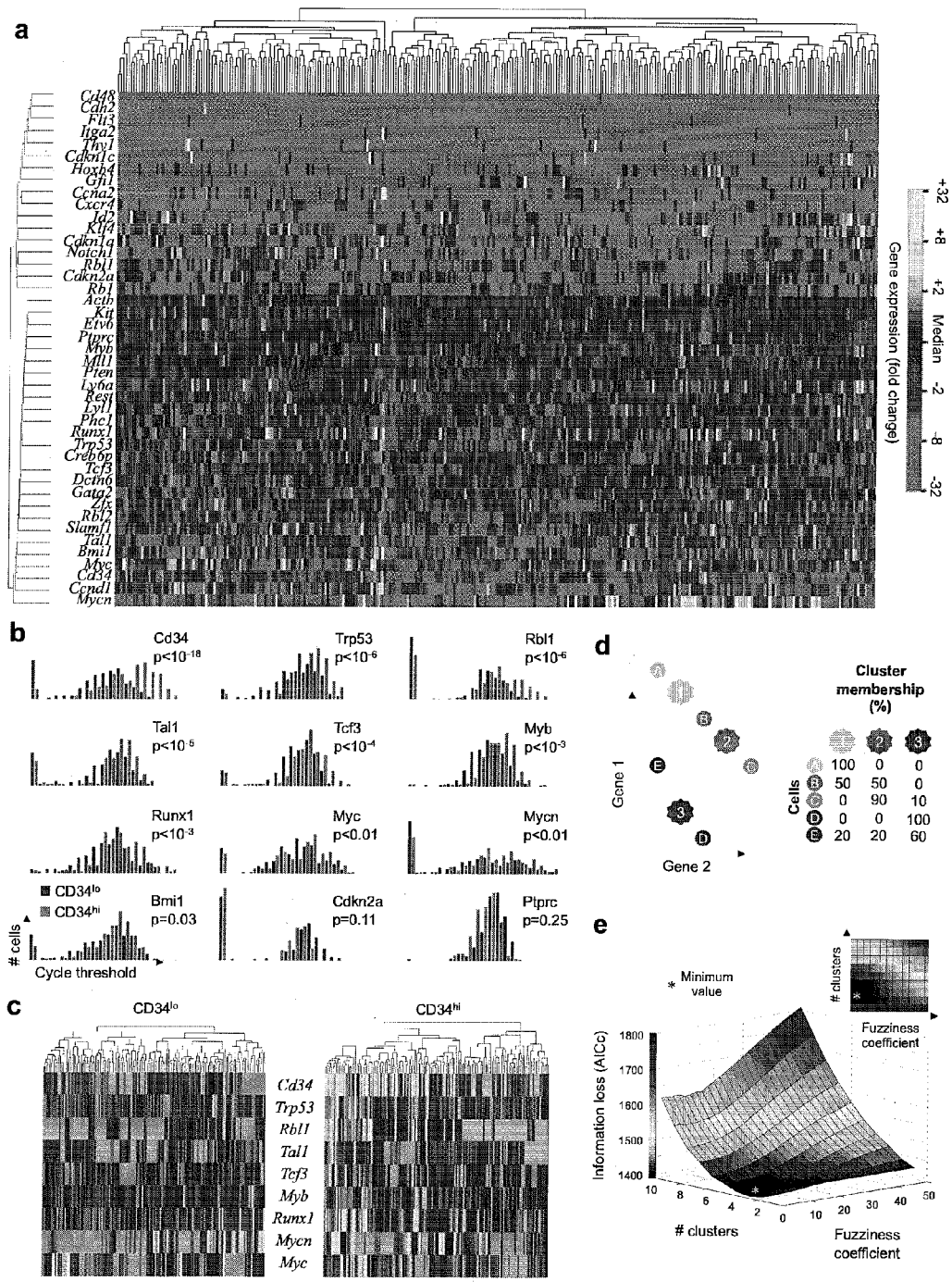
FIG. 8 illustrates an approach for characterization of patterns in higher-order correlated gene expression, consistent with an example embodiment of the present invention.

FIG. 8 shows a multivariate, information-theoretic approach that permits characterization of patterns in higher-order correlated gene expression. (FIG. 8a) Hierarchical clustering of simultaneous expression of 43 genes among 300 individual CD34$^{lo}$ HSCs. Gene expression is presented as fold change from median on a color scale from yellow (high expression, 32-fold above median) to blue (low expression, 32-fold below median). (FIG. 8b) Differentially-expressed genes between CD34$^{lo}$ and CD34$^{hi}$ HSCs, identified using nonparametric two-sample Kolmogorov-Smirnov testing. Nine genes exhibit significantly different ($p<0.01$ following Bonferroni correction for multiple comparisons) distributions of single cell expression between the two populations, illustrated here using median-centered histograms (bin size=0.5 qPCR cycle thresholds). (FIG. 8c) Comparison of CD34$^{lo}$ and CD34$^{hi}$ populations. Cells are clustered hierarchically based on a Kolmogorov-Smirnov-significant gene subset. (FIG. 8d) Individual cells clustered within a hypothetical two-gene space (represented by horizontal and vertical axes). Fuzzy c-means clustering allows shared membership of an individual cell within two or more clusters. Cluster centers (k1, k2, k3) are determined based on the similarities across all cells in the sample. A "fuzziness coefficient" modulates the degree to which partial membership is encouraged among clusters. (FIG. 8e) Iterative application of Akaike Information Criterion (with a second order correction for small sample sizes) to determine optimal clustering parameters. An exhaustive approach was used to determine the information loss (z-axis) associated with different permutations of the number of clusters (y-axis) and the fuzziness coefficient (x-axis). The trough of this plot (grey asterisk) represents the optimal set of clustering parameters for the given data set that will minimize theoretical information loss.

FIG. 9 illustrates optimized partitive modeling of HSC single cell transcriptional data. Fuzzy c-means clustering of HSC single cell transcriptional data using the optimal clustering parameters (3 clusters and a fuzziness coefficient of 1.05). Only the Kolmogorov Smirnov-significant genes (FIG. 8b) are displayed for visual simplicity. Cluster centroids are determined based on partitioning of the CD34$^{lo}$ cells and applied across the other two experimental groups. (FIG. 9a) CD34$^{lo}$ HSCs are relatively evenly distributed across the three clusters. (FIG. 9b) CD34$^{hi}$ HSCs demonstrate a substantially different distribution. Membership in cluster 1 is limited to 4% of the cells and cluster 2 membership is the most common. (FIG. 9c) Side population CD34$^{lo}$ HSCs would be expected to be substantially enriched for HSC capacity and should resemble the CD34$^{lo}$ HSCs. Membership in cluster 1 is significantly expanded, suggesting that cells in this subpopulation are characteristic of highly enriched LT-HSCs.

Further Discussion of Methods for Experimental/Detailed Embodiments

Animals and HSC Isolation 11-week-old male C57BL/6 mice were purchased from Jackson Laboratories (Bar Harbor, Me.). All animal protocols were approved by the Administrative Panel on Laboratory Animal Care at the Stanford University School of Medicine. After euthanasia, femora and tibiae were harvested and the marrow cavities were flushed with 2% fetal bovine serum (FBS) solution. Marrow plugs were dissociated by trituration, filtered through a 70 μm cell strainer, and pelleted by centrifugation. The cell suspension was incubated with biotin-conjugated murine antibodies against lineage surface antigens (CD5, CD45R, CD11b, Gr-1, 7-4, Ter119). After washing, non-labeled cells were extracted from the cell suspension using anti-biotin paramagnetic Micro Beads and the MACS separation system (Miltenyi Biotec, Gladbach, Germany).

FACS Sorting

Lineage-depleted bone marrow cells were sorted using a BD FACSAria equipped with a robotic cloning arm (Becton Dickinson Biosciences, San Jose, Calif.). The following monoclonal antibodies were used in the experiments: CD11b-PECy5 (M1/70; eBioscience), CD45R-PECy5 (RA3-6B2; eBioscience), Gr-1-PECy5 (RB6-8C5, eBioscience), CD8a-PECy5 (53-6.7; eBioscience), CD4-PECy5 (GK1.5; eBioscience), Ter119-PECy5 (TER-119; eBioscience), cKit-AF700 (ACK2; eBioscience), cKit-APC (2B8; BD Pharmigen), cKit-PE (ACK45; BD Pharmigen), Sca-1-APC (D7; BioLegend), Sca-1-FITC (E13-161.7; BD Pharmigen), Sca-1-eFluor605 (D7; eBioscience), CD150-PECy7 (TC15-12F12.2; BioLegend), CD34-Pacific Blue (RAM34; eBioscience), CD34-FITC (RAM34, BD Pharmigen), CD48-PECy5 (HM48-1; BioLegend), CD48-APC (HM48-1; BioLegend), CD135-PECy5 (A2F10; eBioscience). To maximize the fidelity of the single cell sort and exclude unwanted cells, we used restrictive gating based on size and complexity and performed doublet discrimination to exclude aggregated cells. We doubled-sorted the cells, first with high precision four-way purity parameters (yield mask 0/32, purity mask 32/32), followed by a single cell sort using maximal precision parameters (yield mask 0/32, purity mask 32/32 and phase mask 16/32) in order to minimize sorting errors.

Microfluidic Chip-Based Single Cell Analysis

Single cells were sorted into each well of a 96-well plate preloaded with 10 μl of a master mix containing Tris-EDTA buffer (pH 7.0), Superscript III reverse transcriptase enzyme (Invitrogen, Carlsbad, Calif.), Cells Direct reaction mix (Invitrogen, Carlsbad, Calif.), target gene-specific TaqMan assay (primer/probe) sets (Applied Biosystems, Foster City, Calif.) (see Table 1), and SUPERase-In RNAse inhibitor (Applied Biosystems, Foster City, Calif.). Exon-spanning primers were used where possible to avoid amplification of genomic background. Reverse transcription was performed (20 minutes at 50° C., 2 minutes at 95° C.), followed by a 22-cycle pre-amplification (denature at 95° C. for 15 minutes, anneal at 60° C. for 4 minutes, each cycle). Resultant single cell cDNA was mixed with sample loading agent (Fluidigm, South San Francisco, Calif.) and Universal PCR Master Mix (Applied Biosystems, Foster City, Calif.) and loaded into 48.48 Dynamic Array chips (Fluidigm, South San Francisco, Calif.) along with TaqMan assays (Table 1) and assay loading agent (Fluidigm, South San Francisco, Calif.). Products were analyzed on the BioMark reader system (Fluidigm, South San Francisco, Calif.) using a hot start protocol to minimize primer-dimer formation, 30 quantitative PCR cycles were performed.

Statistical Analysis

We designed our analytic approach to perform direct computation of correlations in cell/gene expression at the single cell level and identify groups of cells that exhibited similar patterns of higher-order correlated gene expression, similar to the way in which classical microarray cluster analysis identifies groups of genes that exhibit similar patterns across multiple tissue samples; see Eisen, M. B., Spellman, P. T., Brown, P. O. & Botstein, D., *Cluster analysis and display of genome-wide expression patterns*, Proc Natl Acad Sci USA 95, 14863-14868 (1998).

We utilized a well-established metric for comparison of empirical distributions, the two-sample Kolmogorov-Smirnov (K-S) test, to identify genes whose expression patterns differed significantly between population pairs (FIG. 8b), using a strict cutoff of p<0.01 following Bonferroni correction for multiple samples. Expression data from all chips were normalized relative to the median expression for each gene in the pooled sample and converted to base 2 logarithms. Absolute bounds of +/−5 cycle thresholds (corresponding to 32-fold increases/decreases in expression) were set, and zero-expressers were assigned to this floor.

Figure 10:
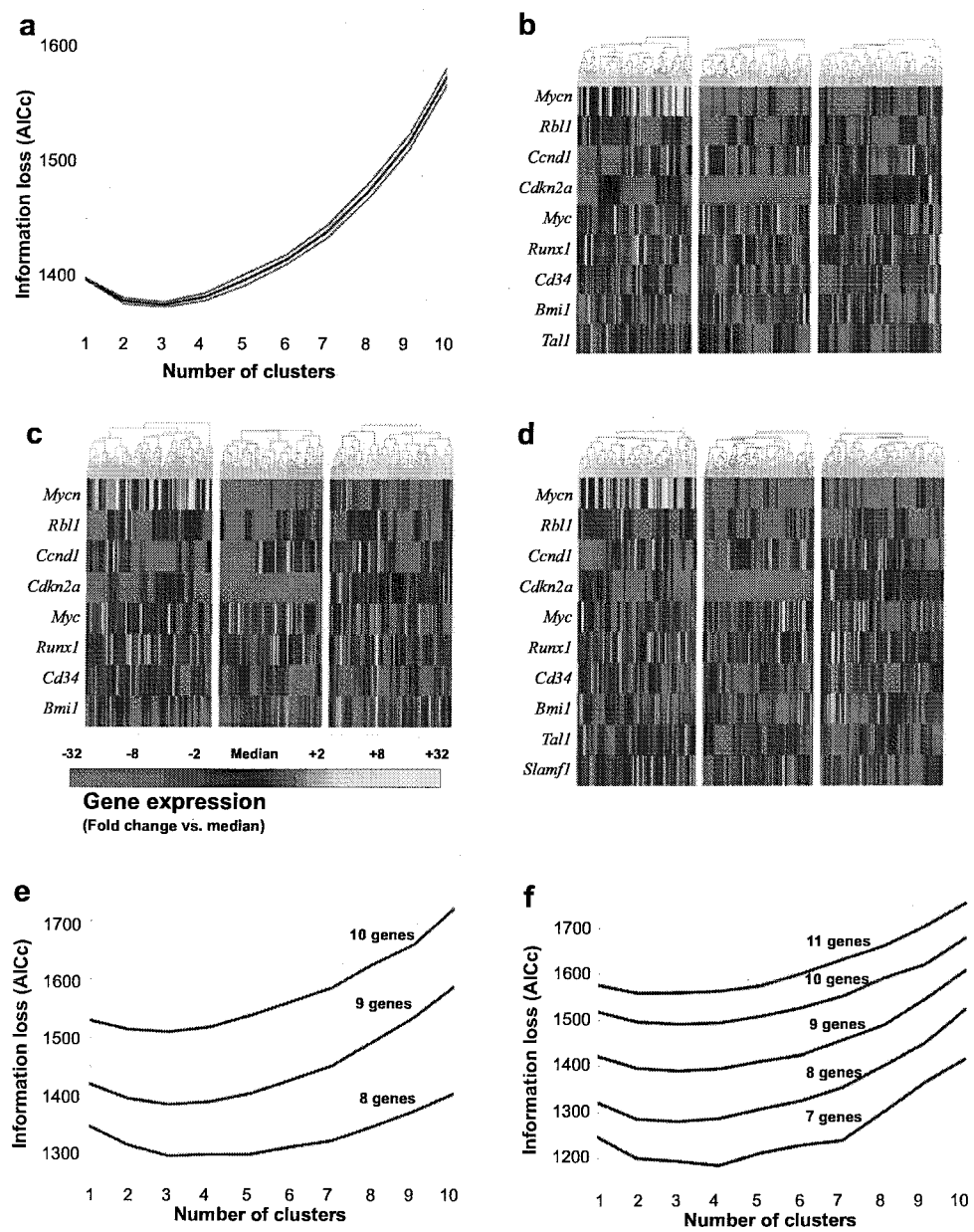
FIG. 10 (via related FIGS. 10a-10f) shows an evaluation of cluster stability, according to an example embodiment of the present invention.

In order to detect overlapping patterns within the single cell transcriptional data, we employed an adaptive fuzzy c-means clustering algorithm for "soft" partitioning. This is a well-established extension of traditional k-means clustering that permits partial membership for each cell in multiple clusters. This allowed explicit overlapping of clusters, as each cell was assigned partial membership to each cluster as dictated by similarities in expression profiles. This method is well suited to the temporal framework of our data, which is essentially a snapshot in time of a dynamic system, and was stable against small perturbations in our dataset (FIG. 10).

All partitive clustering routines are necessarily parametric: that is, they require a priori specification of one or more parameters. We employed an exhaustive optimization scheme using Akaike Information Criterion (AIC) with a second order correction for small sample sizes to evaluate all possible combinations of cluster number and fuzziness coefficient, and selected parameters that minimized the theoretical "information loss" over our data. See Bozdogan H., S.S.L., *Multisample cluster analysis using akaike's information criterion*, Ann. Inst. Statist. Math. 36, 163-180 (1984). Optimally partitioned clusters were then sub-grouped using hierarchical clustering in order to facilitate visualization of data patterning within and across these clusters.

TABLE 1

| Gene ID | Assay ID | Gene ID | Assay ID |
| --- | --- | --- | --- |
| Actb | Mm01205647_g1 | Crebbp | Mm01342435_m1 |
| Klf4 | Mm00516104_m1 | Tal1 | Mm01187033_m1 |
| Rest | Mm00803268_m1 | Lyl1 | Mm00493219_m1 |
| Myc | Mm00487803_m1 | Notch1 | Mm00435249_m1 |
| Mycn | Mm00476449_m1 | Runx1 | Mm01213405_m1 |
| Slamf1 | Mm00443316_m1 | Cdkn1c | Mm00438170_m1 |
| Cd48 | Mm00455932_m1 | Rb1 | Mm00485586_m1 |
| Cd34 | Mm00519283_m1 | Rbl1 | Mm00803251_m1 |
| Flt3 | Mm00438996_m1 | Rbl2 | Mm00487954_m1 |
| Kit | Mm00445212_m1 | Ccnd1 | Mm00432359_m1 |
| Ly6a | Mm00726565_s1 | Ccna2 | Mm01292244_m1 |
| Thy1 | Mm00493681_m1 | Cdkn2a | Mm01257348_m1 |
| Ptprc | Mm00448463_m1 | Cdkn1a | Mm01303209_m1 |
| Itga2 | Mm00434371_m1 | Pten | Mm01212532_m1 |

TABLE 1-continued

| Gene ID | Assay ID | Gene ID | Assay ID |
| --- | --- | --- | --- |
| Etv6 | Mn00468390_m1 | Trp53 | Mm01731287_m1 |
| Bmi1 | Mm00776122_m1 | Id2 | Mm00711781_m1 |
| Gfi1 | Mm00515855_m1 | Cdh2 | Mm00483213_m1 |
| Myb | Mm00501741_m1 | Cxcr4 | Mm01292123_m1 |
| Gata2 | Mm00492301_m1 | Dctn6 | Mm00495994_m1 |
| Hoxb4 | Mm00657964_m1 | *Pou5f1 | Mm00658129_gH |
| Phc1 | Mm01184176_m1 | *Tert | Mm00436931_m1 |
| Tcf3 | Mm01175585_m1 | *Nanog | Mm02019550_s1 |
| Zfx | Mm0234389_g1 | *Cdx4 | Mm00432451_m1 |
| Mll1 | Mn01179237_m1 | *Foxo3 | Mm00490673_m1 |

Table 1 illustrates TaqMan assays used to interrogate gene expression within murine HSCs. All assays were obtained from Applied Biosystems (Foster City, Calif.). It is noted that the assay did not produce exponential amplification, which was excluded from analysis.

TABLE 2

| # Clusters | AIC difference | Akaike weight | Evidence ratio |
| --- | --- | --- | --- |
| 1 | 32.57 | $7.13 \times 10^{-8}$ | $1.18 \times 10^{7}$ |
| 2 | 5.52 | 0.053 | 15.8 |
| 3 | 0 | 0.8445 | 1 |
| 4 | 4.23 | 0.102 | 8.28 |
| 5 | 20.25 | $3.38 \times 10^{-5}$ | $2.50 \times 10^{4}$ |
| 6 | 33.49 | $4.49 \times 10^{-8}$ | $1.88 \times 10^{7}$ |
| 7 | 66.12 | $3.69 \times 10^{-15}$ | $2.29 \times 10^{14}$ |
| 8 | 99.09 | $2.56 \times 10^{-22}$ | $3.29 \times 10^{21}$ |
| 9 | 155.0 | $1.85 \times 10^{-34}$ | $4.57 \times 10^{33}$ |
| 10 | 217.5 | $4.99 \times 10^{-48}$ | $1.69 \times 10^{47}$ |
| 11 | 247.0 | $1.94 \times 10^{-54}$ | $4.34 \times 10^{53}$ |
| 12 | 288.6 | $1.85 \times 10^{-63}$ | $4.57 \times 10^{62}$ |
| 13 | 326.8 | $9.22 \times 10^{-72}$ | $9.16 \times 10^{70}$ |
| 14 | 358.8 | $1.04 \times 10^{-78}$ | $8.13 \times 10^{77}$ |
| 15 | 382.2 | $8.42 \times 10^{-84}$ | $1.00 \times 10^{83}$ |

Table 2 illustrates a likelihood inference and model selection uncertainty. "AIC differences" estimate the relative expected Kullback-Leibler differences between the true (underlying) distribution and that represented by the i-th model (see Kullback, S. & Leibler, R., *On information and sufficiency*, The Annals of Mathematical Statistics, 79-86 (1951)). The predicted best model (in this case, three clusters) will have an AIC difference of zero. Akaike weights correspond to the weight of evidence in favor of a given model being the actual best model (of those evaluated) for the dataset. Evidence ratios permit comparison of the relative likelihood of two models (in terms of Kullback-Leibler information). Here, all evidence ratios are evaluated against the estimated best model (three clusters) using the optimal fuzziness coefficient for each configuration.

Further (Alternative) Detailed Embodiments

In connection with yet further (alternative) detailed embodiments, the present disclosure is directed to prospectively isolating and defining the function of promising LT-HSC subpopulations with highly stem-like transcriptional profiles. It has been discovered that highly selected hematopoietic stem cell populations can be isolated prospectively by defining new surface antigen profiles, and they will display different functional characteristics as compared with each other and the larger HSC population. Understanding that hematopoietic stem cells have been previously characterized in terms of surface antigen expression and function, the principle method used to analyze HSC function is the reconstitution assay, during which single cells or groups of isolated cells are injected into lethally irradiated mice. The protocols and parameters of these assays have been well described and they are readily performed in many laboratories. As such, we devote considerable effort to developing novel combinations (or profiles) of surface antigens in order to purify highly selected populations for this robust analysis.

By defining novel subpopulations of HSCs and prospectively isolating the cells, we can perform novel reconstitution assays with the added advantage of knowing the detailed transcriptional profiles of each cell that are being used to reconstitute, which allows for direct correlation of a given cell's functional performance with its transcriptional program. This correlative information provides for greater understanding of the transcriptional hierarchical organization of HSCs.

Preliminary Data.

In addition to the biological significance associated with characterizing the transcriptional properties of individual subpopulations, this information may also be leveraged to probe for associations with novel surface markers. Each subpopulation as a whole demonstrates an aggregate expression profile for every gene evaluated; however, the magnitude of variation about each of these levels is considerably different for each gene. If we focus on genes whose expression is most stable within each, we can define the subpopulations with many fewer genes. This effectively "opens up" space on the chip for other genes, which allows us to screen for expression of surface antigen genes for each subpopulation of interest.

Such principles are used to develop methods to identify cells from Cluster 2 using a small number of gene markers. In theory, if a small number of genes were sufficient to differentiate between Cluster 2 cells and those from Clusters 1, 3, 4, and 5, then this would add a degree of flexibility to our attempts at developing a prospective isolation technique. The feasibility of this approach is appreciated with consideration to the issue of identifying Cluster 2 cells within the $CD34^{Lo}$ population. In the two sample case, this reduces to the well-described mathematical problem of optimally profiling two non-overlapping sets based on a number of intrinsic features (Peterson and Coleman, 2008). Wilks' lambda testing (a set-based significance measure for classification) can be applied to determine those genes best able to differentiate between Cluster 2 and the other $CD34^{Lo}$ cells. In this regard, reference may be made to FIG. 13A and to Wallace, S. A., Anderson, D. I., Anderson, D., Mayo, A. M., Nguyen, K. T., and Ventre, M. A., *Motor performance with a simulated artificial limb*, Percept Mot Skills, 88, 759-764 (1999).

Figure 13:
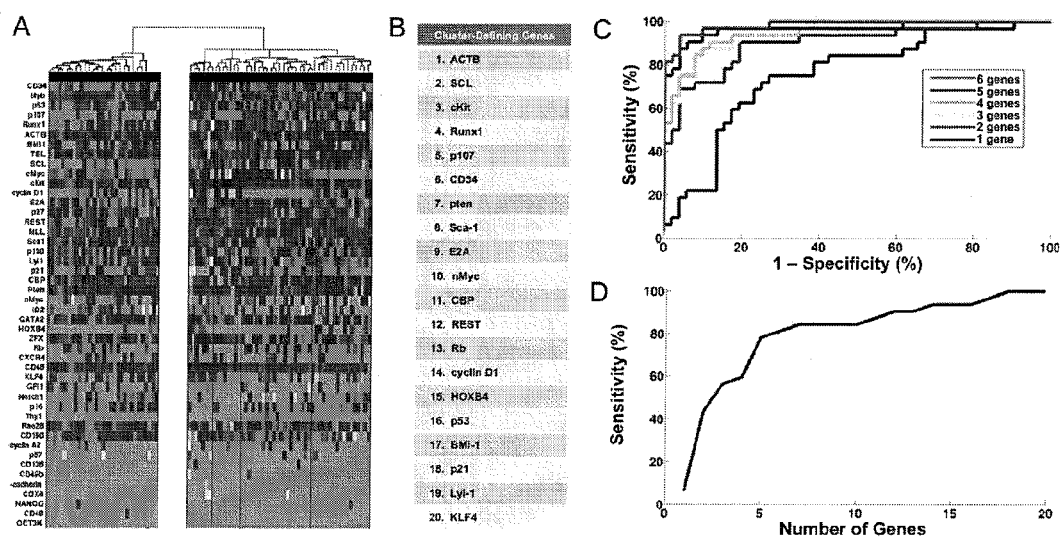
FIGS. 13a-d depict linear discriminant analysis (LDA) for CD 34$^{lo}$ HSCs (hematopoietic stem cells), according to example embodiments of the present invention. a. Cluster 2 cells (left) were compared against the aggregate set of cells from clusters 1, 3, 4, and 5 (right). b. Individual genes ranked according to their ability to discriminate between these two groups c. Groups of genes (i.e., best "1 gene" or best "3 gene" combination) were evaluated using ROC analysis. Each ROC curve represents the trade-off between sensitivity and specificity. As expected, more accurate classification is achieved with a larger number of genes. d. Maximum achievable sensitivity with specificity fixed at 100% for each number of genes.

This methodology allows genes to be ranked individually according to their ability to distinguish these cells, e.g., as seen in FIG. 13B. A linear-discriminant analysis (LDA) algorithm is then applied to identify the maximum separation of groups about a linear hyperplane. For background information in this regard, reference may be made to Peterson, L. E., and Coleman, M. A., *Machine learning-based receiver operating characteristic (ROC) curves for crisp and fuzzy classification of DNA microarrays in cancer research*, Int J Approx Reason 47, 17-36 (2008). This provides a partitioning scheme to classify cells into either of the two groups based on gene expression. The accuracies of the resulting models can be reviewed and confirmed using traditional receiver operating characteristic (ROC) analysis. For identifying the minimal subset of genes capable of efficiently isolating Cluster 2 cells, an ROC curve is first constructed using only one gene (ACTB), and the process proceeds by increasing the number of genes one at a time (using an automated Wilks' lambda cost function), constructing additional curves with the addition of each gene as exemplified in FIG. 13C. FIG. 13C illustrates the maximum achievable sensitivity associated with 100% specificity for each gene number. Surprisingly, these data indicate that with as few as 18 properly selected genes, the same clustering efficiency as with all 48 can be achieved. This means that the 30 free channels of the microfluidic chip can be used to explore other surface antigens previously studied in HSC biology and other cell types. Using this strategy, we predict that if HSCs express even a small fraction of all known surface antigen genes, than this approach has an excellent chance of detecting novel patterns of surface marker expression within these subpopulations. Furthermore, one can thereby easily determine whether novel combinations of surface antigens would increase the efficiency of sorts for these discrete clusters. Since we do not have to modify our experimental protocol to perform these studies and because our preliminary data demonstrate such tight correlations, advantages of this strategy include the ability to improve the efficiency of sorting for subpopulations of LT-HSCs. As such, this approach is relatively low risk. This approach relates to and can be the foundation of the studies in connection with the experimental embodiments (or designs) in the immediately-following discussion. However, we will also attempt to raise novel monoclonal antibodies against unique antigens produced by subpopulation cells, which is a more speculative approach. These two strategies, one low risk and one more speculative, will yield important advances in the isolation of HSC subpopulations.

Experimental Embodiment/Design

In connection with a related experimental embodiment, a two-pronged approach is used to develop protocols to prospectively isolate HSC subpopulations. Linear discriminant analysis (LDA) is applied to the preliminary LT-HSC data (described herein) in order to identify a minimal transcriptional signature capable of distinguishing a subgroup of interest from the remaining cells. This classification scheme is then leveraged to determine novel combinations of known surface antigens that are most strongly associated with this subpopulation. After we have identified novel marker profiles, we may prospectively isolate subpopulations of interest and perform any number of standard functional analyses. By demonstrating the functional characteristics of each subpopulation, we expect to define the functional/phenotypic significance of the subpopulations that we identify using the high-throughput single cell transcriptional analysis that is the foundation of this proposal.

To screen for novel surface marker combinations using single cell analysis, various methods can be used. We wish to leverage the information from our initial cluster analysis to generate meaningful likelihood predictions about the origins of and relationships among individual cells in order to direct our search for potential surface marker combinations capable of prospectively isolating the LT-HSC subpopulation. This is achieved through recursive application of fuzzy c-means clustering and linear discriminant analysis (LDA), as detailed in FIG. 14 and below under: Define cells of interest, Training phase, Optimized classification scheme, Transcriptional evaluation, and FACS evaluation.

Define Cells of Interest.

Figure 14:
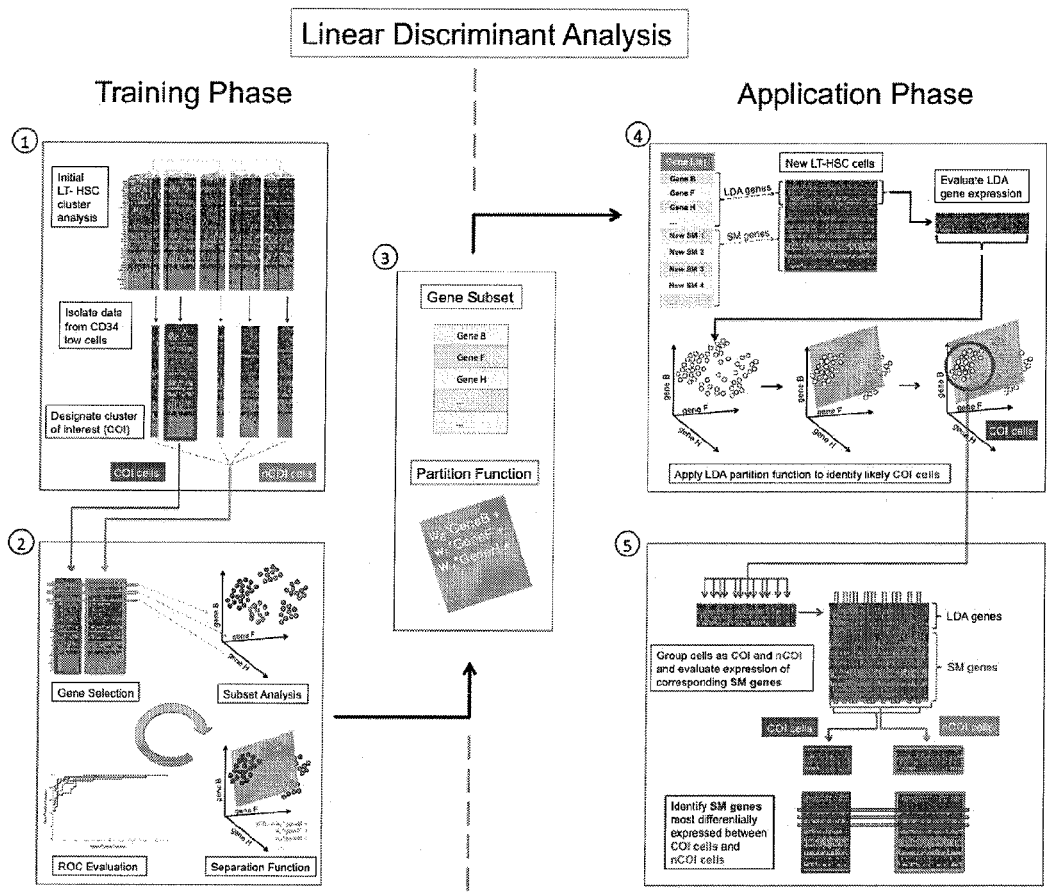
FIG. 14 shows discriminant analysis (LDA) schema, according to another example embodiment of the present invention.

The cluster designations previously ascribed to our LT-HSC data will be flattened, or "defuzzified," by assigning to each cell the single cluster with which it associates the highest membership. This allows us to group gene expression data into two mutually exclusive and complementary sets: those cells that fall into cluster 2 and those that do not (i.e., cells belonging to clusters 1, 3, 4, or 5). We will refer to the former group as our "Cluster of Interest" (COI), and the latter as "not COI" or nCOI. Only cells from the CD34 low fraction will be considered. The remainder of our analysis will focus on recapitulating the distinctive features of these two groups using limited transcriptional information (FIG. 14.1).

Linear Discriminant Analysis (Training Phase).

LDA will be applied to the 48 gene expression data from cells in each class (COI and nCOI) to determine those genes whose expression patterns maximally differ between these two groups. By exploiting the covariate nature of our data, LDA is capable of identifying not only individual genes but also gene combinations with maximum differentiating capacity. This is achieved through an iterative process, with each pass evaluating one specific combination of genes. Evaluating all gene combinations individually would require $$\sum_{i=1}^{48} {}_{48}C_i (\sim 10^{14}) \text{ analyses.}$$

In computational complexity theory, this constitutes an NP-complete problem (i.e., one whose solution cannot be determined in polynomial ["P"] time). Thus we employ a stepwise implementation of the Wilks lambda cost function (F-value thresholds of 2 and 1 to add or remove a gene) to guide selection of gene combinations and reduce computational load. For each gene set:

COI and nCOI cells are compared based on their expression of the specific subset of genes (FIG. 14.2, top-left). In the simplified 3 gene case, this corresponds to examining spheres (individual cells) in 3-space, where each axis corresponds to a single gene (FIG. 14.2, top-right).

LDA determines the plane that maximally separates cells of one group from the other (FIG. 14.2, bottom-right). Mathematically, this is described by a separation function corresponding to a weighted sum of the expressions of each selected gene. In the general case (n genes), this is equivalent to maximizing binary separation in n-space, and the partition function assumes the form of a linear hyperplane.

Receiver operating characteristic (ROC) analysis is employed to evaluate the appropriateness of our partition function. Generally speaking, a hyperplane may be manipulated along its orthogonal axis (akin to stacking planes "in parallel") by adjusting the constant term of its characteristic equation. Biologically, this corresponds to varying the specificity or sensitivity of a classification scheme without changing the relative weightings of each gene. Thus, instead of identifying a single measure of accuracy, an LDA is characterized by a set of sensitivity and specificity pairs. The union of all such pairs constitutes the basis for an ROC curve (FIG. 14.2, bottom-left), and ROC analysis evaluates the area under these curves as a proxy for optimality of partitioning (FIG. 14.2, bottom-left).

Optimized Classification Scheme.

The end result of a "trained" LDA is a feature subset (in this case, 8-10 genes) and a corresponding partition function. The partition function provides a heuristic for the classification of future (unknown) cells on the basis solely of expression of genes in this subset (FIG. 14.3).

Linear discriminant analysis can be used, e.g., as an application to novel surface marker chips. In order to evaluate the efficacy of various surface markers, additional microfluidic single cell analyses will be performed on murine BM-derived LT-HSCs (CD34 low fraction), as described in Specific Aim 1 Here, the microfluidic chip will be modified to interrogate those genes selected by our LDA, with the remaining genes replaced by candidate surface markers drawn from the known pool of cluster differentiating (CD) genes. Our preliminary data suggest that 18 genes will be required to define COI cells, in which case 30 slots per chip would be available to investigate these novel markers. As nearly 400 such markers (see Zola, H., Swart, B., Nicholson, I., Aasted, B., Bensussan, A., Boumsell, L., Buckley, C., Clark, G., Drbal, K., Engel, P., et al., *CD molecules: human cell differentiation molecules*, Blood 106, 3123-3126 (2005)), we anticipate that up to 15 distinct microfluidic chip configurations will be required to evaluate all markers (n=2 chips per distinct gene list [30 total chips]).

The gene set for each chip will consist of ~18 known genes from the LDA and ~30 surface markers; and the resulting data are evaluated first solely on the basis of the 18 LDA genes (FIG. 14.4, top).

The partition function (determined previously) is then used to classify each new cell as either COI or nCOI on the basis of expression of these 8 genes (FIG. 14.4, bottom).

Transcriptional Evaluation of Surface Markers.

Once each cell has been classified as either COI or nCOI, the expression profiles of the remaining 30 genes are then compared for these two groups, again using LDA. Here, LDA is used to identify those surface marker genes whose expression is best able to distinguish these two groups.

FACS Evaluation of Surface Markers.

Each candidate surface marker determined above will be evaluated over additional murine HSCs using microfluidic analysis, whereby the marker in question is appended to the LT-HSC FACS sort prior to single cell analysis (n=3 chips per marker). The resulting data will be fed into our initial fuzzy c-means clustering (using the prior, fixed cluster centroids) and the fraction of cells falling into COI will be determined. Combinations of markers will be applied subjectively on the basis of LT-HSC isolation fraction in order to determine that best capable of prospectively identifying these cells.

It will be understood by those skilled in the relevant art that the herein-described implementations are merely exemplary, and many changes can be made without departing from the true spirit and scope of the present invention. Therefore, it is intended by the appended claims to cover all such changes and modifications that come within the true spirit and scope of this invention.

What is claimed is:

1. A method for comparing gene expression, comprising:
isolating a plurality of single cells in a first cell population and a plurality of single cells in a second cell population;
choosing at least two individual genes to analyze an expression of the genes within the single cells of each of the first cell population and second cell population;
for each of the gene expressions of the first and second cell populations, determining a transcriptional identity of a single cell of the plurality of single cells based on individual gene expression of the at least two genes within the single cell;
for each of the first and second cell populations, using the transcriptional identity of each of the single cells to determine a heterogeneity profile; and
using a logic circuit to perform statistical analysis to compare the heterogeneity profile of the first cell population to the heterogeneity profile of the second cell population, the comparison determining the similarity between the first and second cell populations.

2. A method of comparing gene expression, comprising:
isolating a plurality of single cells in a cell population;
choosing at least two genes to analyze an expression of each gene within each of the single cells;
determining a transcription identity of a single cell of the plurality of single cells based on gene expression of the at least two genes;
using a logic circuit to perform a statistical cluster analysis on the transcriptional identity of each of the single cells of the plurality of single cells to determine whether the cell population includes one or more subpopulations;
determining a heterogeneity profile of the one or more subpopulations; and
using a second logic circuit to perform a divergence-based statistical analysis to compare the heterogeneity profiles of the one or more subpopulations to determine whether the one or more subpopulations are distinct subpopulations.

3. A method for comparing gene expression, comprising:
isolating a plurality of single cells in a first cell population;
choosing at least two genes to analyze an expression of each gene within each of the single cells;
determining a transcription identity of a single cell of the plurality of single cells based on gene expression of the at least two genes;
using the transcriptional identity of the single cells to determine whether the first cell population includes one or more subpopulations;
using a logic circuit to perform cluster analysis based on the transcriptional identity of each of the single cells of the plurality of single cells to determine whether the first cell population includes one or more subpopulations;
determining a heterogeneity profile of the one or more subpopulations;
using the logic circuit to perform a divergence-based statistical analysis to compare the heterogeneity profiles of the one or more subpopulations to determine whether the one or more subpopulations are distinct subpopulations;
determining a total heterogeneity profile for the first cell population; and
using the logic circuit to perform statistical analysis to compare the total heterogeneity profile of the first cell population to a previously determined heterogeneity profile of a second cell population.

4. A method for comparing gene expression of a first cell population, comprising:
using a logic circuit to:
determine a transcriptional identity for each individual cell in the first cell population, the transcriptional identity based on a level of gene expression of at least two genes;
perform cluster analysis, based on the transcriptional identity of each individual cell, to determine whether the first cell population includes one or more subpopulations;
determine a heterogeneity profile of the one or more subpopulations and compare the heterogeneity profiles of the one or more subpopulations to determine whether the one or more subpopulations are distinct subpopulations;
determine a total heterogeneity profile for the first cell population; and perform a divergence-based statistical analysis to compare the total heterogeneity profile of the first cell population to a previously determined heterogeneity profile of a second cell population.

5. The method of claim 1, wherein using the logic circuit to perform statistical analysis includes utilizing a divergence analysis to determine an amount of divergence between probability distributions of the heterogeneity profile of the first cell population to the heterogeneity profile of the second cell population.

6. The method of claim 5, wherein utilizing the divergence analysis includes determining whether the heterogeneity profile of the first cell population to the heterogeneity profile of the second cell population are highly divergent thereby indicating distinctness of the first cell population and the second cell population.

7. The method of claim 1, wherein using the logic circuit to perform statistical analysis includes utilizing a Kullback-Leibler divergence analysis to determine an amount of divergence between probability distributions of the heterogeneity profile of the first cell population and the heterogeneity profile of the second cell population.

8. The method of claim 1, further including utilizing a phi-entropy based divergence analysis to determine the transcriptional identity of each of the single cells to determine the heterogeneity profile.

9. The method of claim 1, further including utilizing the logic circuit to compare a heterogeneity profile of at least one of the first cell population and the second cell population to a previously determined heterogeneity profile for the population to determine whether at least one of the first cell population and the second cell population has changed over time.

10. The method of claim 2, wherein determining the heterogeneity profile of the one or more subpopulations includes utilizing a phi-entropy based divergence analysis to determine the transcriptional identity of each of the single cells to determine the heterogeneity profile.

11. The method of claim 2, wherein utilizing the divergence-based statistical analysis includes determining an amount of divergence between probability distributions of a heterogeneity profile of a first cell population and a heterogeneity profile of a second cell population.

12. The method of claim 11, wherein utilizing the divergence-based statistical analysis includes determining whether the heterogeneity profile of the first cell population and the heterogeneity profile of the second cell population are highly divergent, thereby indicating distinctness of the first cell population and the second cell population.

13. The method of claim 3, wherein using the logic circuit to perform the divergence-based statistical analysis includes determining an amount of divergence between probability distributions of the heterogeneity profile of the first cell population and the heterogeneity profile of the second cell population.

14. The method of claim 13, wherein utilizing the divergence-based statistical analysis includes determining whether the heterogeneity profile of the first cell population and the heterogeneity profile of the second cell population are highly divergent thereby indicating distinctness of the first cell population and the second cell population.

15. The method of claim 4, wherein using the logic circuit to perform the divergence-based statistical analysis includes utilizing a divergence analysis to determine an amount of divergence between probability distributions of the heterogeneity profile of a first cell population to the heterogeneity profile of a second cell population.

* * * * *